United States Patent
Park et al.

(10) Patent No.: US 11,793,482 B2
(45) Date of Patent: Oct. 24, 2023

(54) ULTRASOUND IMAGING APPARATUS, METHOD OF CONTROLLING THE SAME, AND COMPUTER PROGRAM PRODUCT

(71) Applicant: SAMSUNG MEDISON CO., LTD., Hongcheon-gun (KR)

(72) Inventors: Taejin Park, Seongnam-si (KR); Summo Yang, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 139 days.

(21) Appl. No.: 16/566,306

(22) Filed: Sep. 10, 2019

(65) Prior Publication Data
US 2020/0178928 A1    Jun. 11, 2020

(30) Foreign Application Priority Data
Dec. 11, 2018   (KR) .................. 10-2018-0159092

(51) Int. Cl.
*A61B 8/00*   (2006.01)
*A61B 8/08*   (2006.01)
(Continued)

(52) U.S. Cl.
CPC .............. *A61B 8/0841* (2013.01); *A61B 8/14* (2013.01); *A61B 8/463* (2013.01); *A61B 8/465* (2013.01);
(Continued)

(58) Field of Classification Search
CPC ......... A61B 8/0841; A61B 8/14; A61B 8/463; A61B 8/5292; A61B 8/54; A61B 8/461;
(Continued)

(56) References Cited

U.S. PATENT DOCUMENTS 9,226,731 B2    1/2016  Liu et al.
9,706,978 B2    7/2017  Baek et al.
(Continued)

FOREIGN PATENT DOCUMENTS

KR    10-1511299 B1    4/2015
KR    10-1770406 B1    8/2017
(Continued)

OTHER PUBLICATIONS

GE Healthcare, "GE Healthcare LOGIQ E9 ultrasound Volume Navigation image examples", Jun. 15, 2011, YOUTUBE, Retrieved from https://www.youtube.com/watch?=eXPC4Pz8L1g, 3 minutes and 27 seconds.
(Continued)

*Primary Examiner* — Christopher Koharski
*Assistant Examiner* — Taylor Deutsch
(74) *Attorney, Agent, or Firm* — Sughrue Mion, PLLC

(57) ABSTRACT

Provided are an ultrasound imaging apparatus and a method of controlling the same. The ultrasound imaging apparatus includes: a probe configured to transmit ultrasound signals to an object and receive echo signals corresponding to the ultrasound signals; a display; and at least one processor configured to detect a reference region of a medical tool inserted into the object in an ultrasound image generated based on the echo signals, control the display to display at least one distance-indicating line arranged with respect to the reference region in the ultrasound image, and update a position of the at least one distance-indicating line according to movement of the medical tool.

12 Claims, 18 Drawing Sheets

(51) Int. Cl.
*A61B 8/14* (2006.01)
*A61B 17/34* (2006.01)

(52) U.S. Cl.
CPC .............. *A61B 8/5292* (2013.01); *A61B 8/54* (2013.01); *A61B 2017/3413* (2013.01)

(58) Field of Classification Search
CPC ......... A61B 8/44; A61B 8/4427; A61B 8/565; A61B 8/464; A61B 8/465; A61B 2017/3413
See application file for complete search history.

(56) References Cited

U.S. PATENT DOCUMENTS

| | | | |
|---|---|---|---|
| 2005/0159676 A1* | 7/2005 | Taylor | A61B 10/0275 |
| | | | 600/567 |
| 2008/0033293 A1* | 2/2008 | Beasley | A61B 8/465 |
| | | | 600/437 |
| 2010/0217117 A1 | 8/2010 | Glossop et al. | |
| 2010/0298705 A1* | 11/2010 | Pelissier | A61B 8/42 |
| | | | 600/443 |
| 2011/0009748 A1 | 1/2011 | Greene et al. | |
| 2012/0289820 A1 | 11/2012 | Rohling | |
| 2013/0197357 A1* | 8/2013 | Green | A61B 6/12 |
| | | | 600/424 |
| 2014/0128771 A1 | 5/2014 | LaConte et al. | |
| 2015/0272700 A1* | 10/2015 | Masuda | A61B 34/20 |
| | | | 600/424 |
| 2016/0120510 A1 | 5/2016 | Burbank et al. | |
| 2016/0346004 A1 | 12/2016 | Rahman | |
| 2017/0202626 A1* | 7/2017 | Kula | A61B 34/20 |
| 2017/0245838 A1* | 8/2017 | Munrow | A61B 10/0045 |
| 2018/0103938 A1 | 4/2018 | Stoianovici et al. | |
| 2018/0116643 A1 | 5/2018 | Bang et al. | |

FOREIGN PATENT DOCUMENTS

| | | |
|---|---|---|
| KR | 10-2018-0046675 A | 5/2018 |
| WO | 2015023665 A1 | 2/2015 |

OTHER PUBLICATIONS

Communication dated Apr. 3, 2020, from the European Patent Office in counterpart European Application No. 19197119.1.
Communication issued by the European Patent Office dated Feb. 1, 2023 in European Patent Application No. 19197119.1.

* cited by examiner

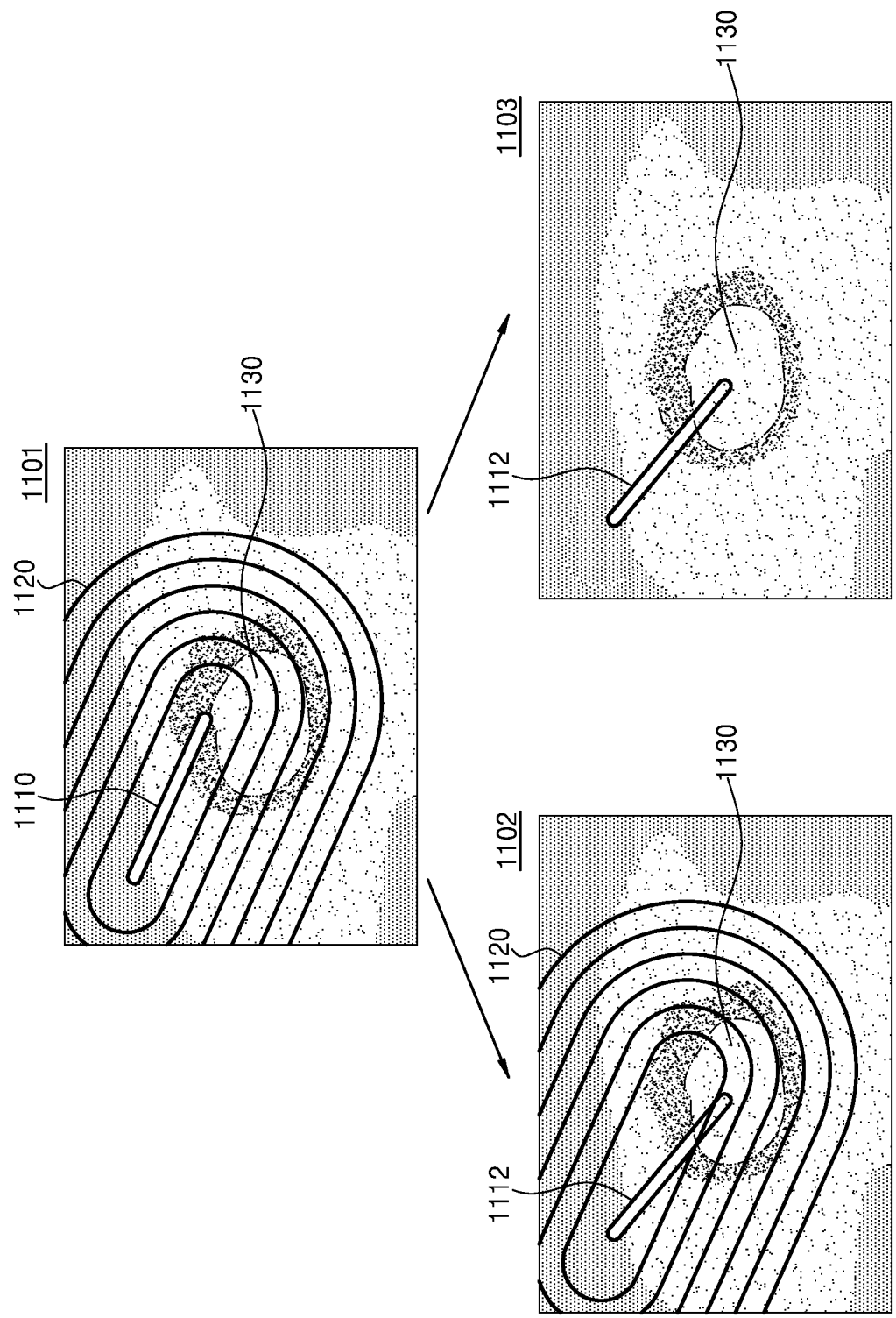

ULTRASOUND IMAGING APPARATUS, METHOD OF CONTROLLING THE SAME, AND COMPUTER PROGRAM PRODUCT

CROSS-REFERENCE TO RELATED APPLICATION(S)

This application is based on and claims priority under 35 U.S.C. § 119 to Korean Patent Application No. 10-2018-0159092, filed on Dec. 11, 2018, in the Korean Intellectual Property Office, the disclosure of which is incorporated by reference herein in its entirety.

BACKGROUND

1. Field

The disclosure relates to ultrasound imaging apparatuses, and more particularly, to ultrasound imaging apparatuses for displaying at least one distance-indicating line.

2. Description of Related Art

Ultrasound diagnostic apparatuses transmit ultrasound signals generated by transducers of a probe to an object and detect information about signals reflected from the object, thereby obtaining at least one image of an internal part, for example, soft tissue or blood flow, of the object.

SUMMARY

Provided are ultrasound imaging apparatuses and methods of controlling the same, which are capable of displaying at least one distance-indicating line with respect to a medical tool according to movement of the medical tool, and computer program products.

Additional aspects will be set forth in part in the description which follows and, in part, will be apparent from the description, or may be learned by practice of the presented embodiments.

In accordance with an aspect of the disclosure, an ultrasound imaging apparatus includes: a probe configured to transmit ultrasound signals to an object and receive echo signals corresponding to the ultrasound signals; a display; and at least one processor configured to detect a reference region of a medical tool inserted into the object in an ultrasound image generated based on the echo signals, control the display to display at least one distance-indicating line arranged with respect to the reference region in the ultrasound image, and update a position of the at least one distance-indicating line according to movement of the medical tool.

The at least one processor may be further configured to control the display to display the at least one distance-indicating line at set intervals with respect to the reference region of the medical tool.

The at least one processor may be further configured to control the display to display distance information about a distance from the reference region of the medical tool to each of the at least one distance-indicating line.

The reference region of the medical tool may be at least a portion of the medical tool including a region where a distal end of the medical tool is located, and the at least one processor may be further configured to control the display to display the at least one distance-indicating line according to its distance from a border of the reference region or from a center of the reference region.

The at least one processor may be further configured to control the display to visually display the reference region of the medical tool and fixedly display, in response to reception of an input of fixing a distance-indicating line, the at least one distance-indicating line currently being displayed, regardless of the movement of the medical tool.

The at least one processor may be further configured to control the display to visually display the reference region of the medical tool and hide, in response to reception of an input of hiding a distance-indicating line, the at least one distance-indicating line currently being displayed.

The at least one processor may be further configured to provide a user interface for setting at least one of conditions for respectively setting at least one of the number of the at least one distance-indicating line, a shape of the at least one distance-indicating line, an interval between the at least one distance-indicating line, and the reference region of the medical tool.

The condition for setting the reference region of the medical tool may include at least one from among a width, an area and a shape of the reference region and whether to set the reference region as a dot.

The shape of the at least one distance-indicating line may include at least one from among a color, a transparency, and a pattern of the at least one distance-indicating line, and a transparency with respect to a distance of each of the at least one distance-indicating line from the reference region of the medical tool.

The at least one processor may be further configured to control the display to display at least one distance-indicating line arranged with respect to a preset region in the ultrasound image.

The at least one processor may be further configured to control the display to visually display at least one region of interest (ROI) in the ultrasound image and display distance information about a distance from the reference region of the medical tool to each of the at least one ROI.

The at least one processor may be further configured to control the display to display an extension line extending a long axis of the medical tool and display at least one of a line connecting a distal end of the medical tool to each of at least one ROI, distance information about a distance from the distal end of the medical tool to each of the at least one ROI, and information about a shortest distance from the extension line to each of the at least one ROI.

In accordance with another aspect of the disclosure, a method of controlling an ultrasound imaging apparatus includes: detecting a reference region of a medical tool inserted into an object in an ultrasound image of the object; displaying at least one distance-indicating line arranged with respect to the reference region in the ultrasound image; and updating a position of the at least one distance-indicating line according to movement of the medical tool.

In accordance with another aspect of the disclosure, a computer program product includes a recording medium having stored therein instructions for performing: detecting a reference region of a medical tool inserted into an object in an ultrasound image of the object; displaying at least one distance-indicating line arranged with respect to the reference region in the ultrasound image; and updating a position of the at least one distance-indicating line according to movement of the medical tool.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 11 is a diagram for explaining operations of an ultrasound imaging apparatus in a distance-indicating line fixed mode and in a distance-indicating line hidden mode, according to an embodiment of the disclosure;

DETAILED DESCRIPTION

Figure 1:
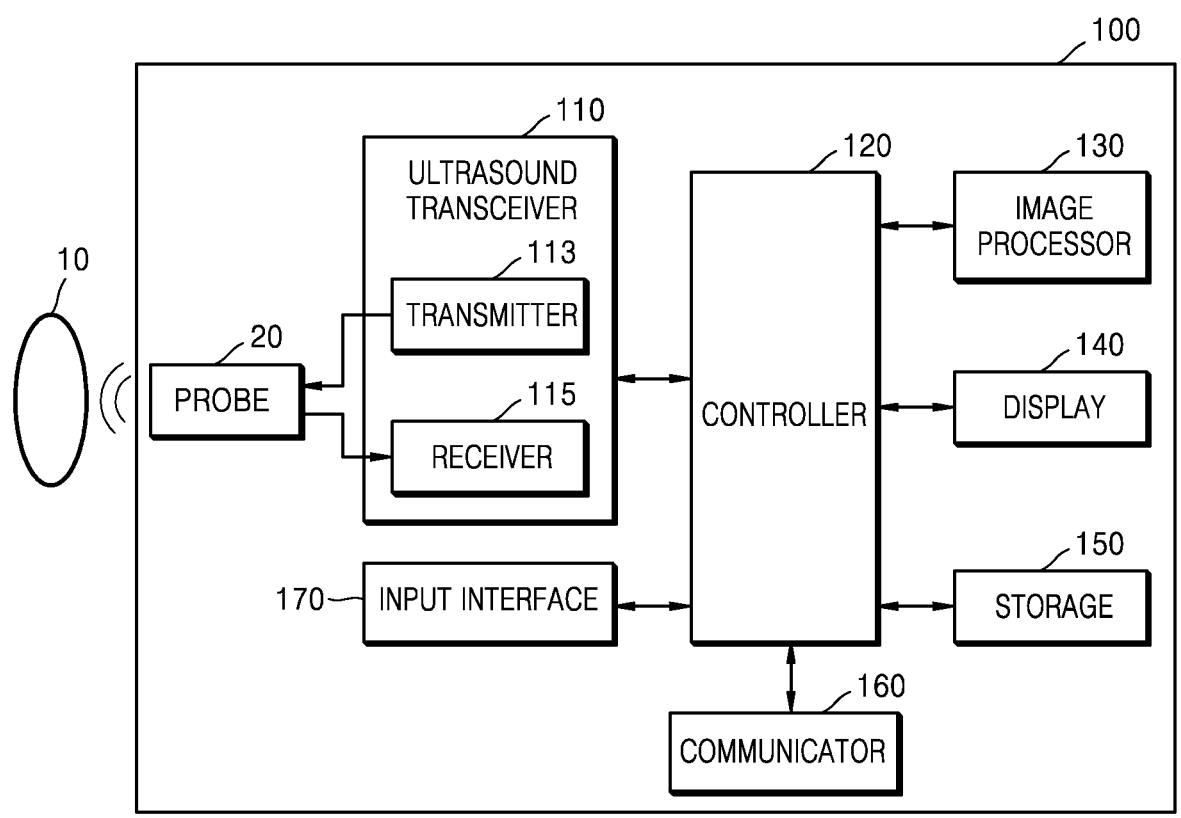
FIG. 1 is a block diagram illustrating an ultrasound imaging apparatus according to an embodiment of the disclosure.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements. Expressions such as "at least one of," when preceding a list of elements, modify the entire list of elements and do not modify the individual elements of the list.

In exemplary embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or tissue, or a phantom.

Throughout the specification, an ultrasound image refers to an image of an object processed based on ultrasound signals transmitted to the object and reflected therefrom.

In the present specification, a 'medical tool' refers to a tool that is inserted into an object during a medical activity. Examples of the medical tool may include a medical needle, a biopsy needle, a tube, a catheter, etc. The type of medical tool is not limited to the above-described examples, and may include various tools.

Throughout the specification, an 'ultrasound imaging apparatus' may be used interchangeably with an 'ultrasound diagnosis apparatus.'

Hereinafter, embodiments will be described in more detail with reference to the accompanying drawings.

FIG. 1 is a block diagram illustrating a configuration of an ultrasound imaging apparatus 100, i.e., a diagnostic apparatus, according to an exemplary embodiment.

Referring to FIG. 1, the ultrasound imaging apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound imaging apparatus 100 may be of a cart-type or a portable-type ultrasound imaging apparatus, which is portable, moveable, mobile, or hand-held. Examples of a portable-type ultrasound imaging apparatus may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmitting signals received by the probe 20, from a transmitter 113. The plurality of transducers may receive ultrasound signals reflected from the object 10 to generate reception signals. In addition, the probe 20 and the ultrasound imaging apparatus 100 may be formed in one body (e.g., disposed in a single housing), or the probe 20 and the ultrasound imaging apparatus 100 may be formed separately (e.g., disposed separately in separate housings) but linked wirelessly or via wires. In addition, the ultrasound imaging apparatus 100 may include one or more probes 20 according to embodiments.

The controller 120 may control the transmitter 113 for the transmitter 113 to generate transmitting signals to be applied to each of the plurality of transducers based on a position and a focal point of the plurality of transducers included in the probe 20.

The controller 120 may control an ultrasound receiver 115 to generate ultrasound data by converting reception signals received from the probe 20 from analog to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound imaging apparatus 100. The ultrasound imaging apparatus 100 may include two or more displays 140 according to the present exemplary embodiment. The display 140 may include a touch screen in combination with a touch panel.

The controller 120 may control the operations of the ultrasound imaging apparatus 100 and flow of signals between the internal elements of the ultrasound imaging apparatus 100. The controller 120 may include a memory for storing a program or data to perform functions of the ultrasound imaging apparatus 100 and a processor and/or a microprocessor (not shown) for processing the program or data. For example, the controller 120 may control the operation of the ultrasound imaging apparatus 100 by receiving a control signal from the input interface 170 or an external apparatus.

The ultrasound imaging apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound imaging apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound imaging apparatus 100 may process the data of the external apparatus in response to the control signal of the controller 120 received via the communicator 160.

A program for controlling the ultrasound imaging apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound imaging apparatus 100, input and/or output ultrasound data, ultrasound images, applications, etc.

The input interface 170 may receive a user's input to control the ultrasound imaging apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound imaging apparatus 100 according to the present exemplary embodiment is described below with reference to FIGS. 2A, 2B, and 2C.

Figure 2A:
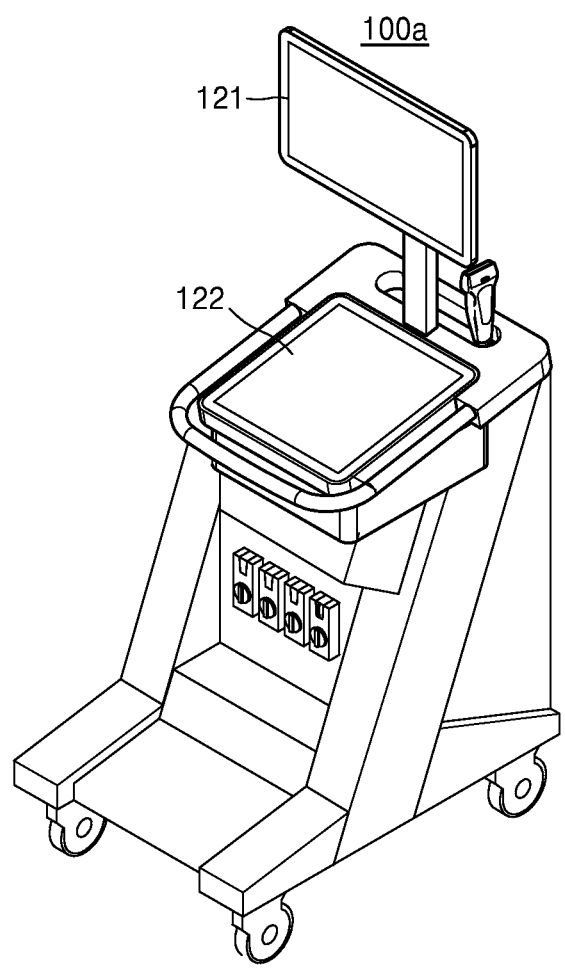
FIGS. 2A, 2B, and 2C are diagrams respectively illustrating an ultrasound imaging apparatus according to an embodiment of the disclosure.
Figure 2B:
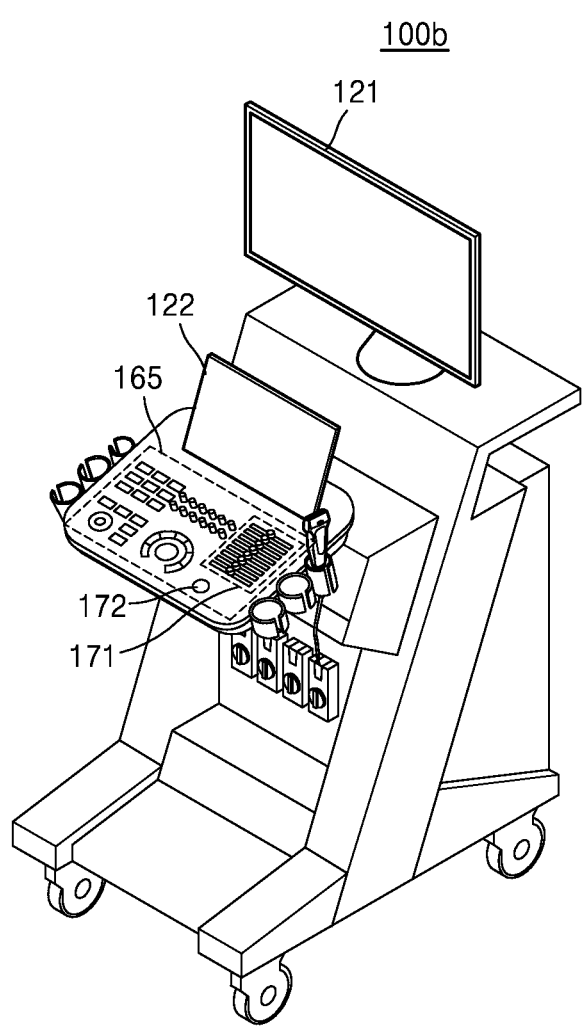
Figure 2C:
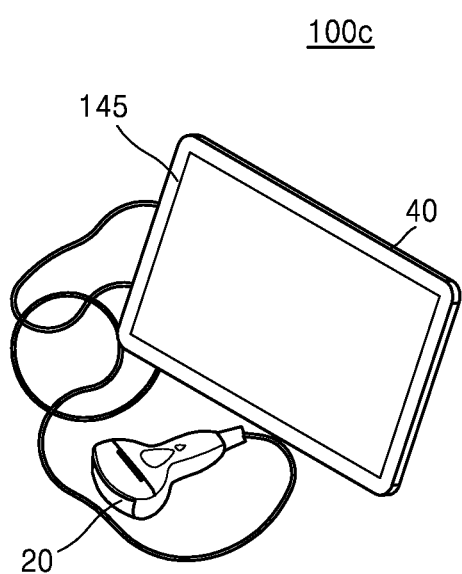

FIGS. 2A, 2B, and 2C are diagrams illustrating ultrasound imaging apparatus according to an exemplary embodiment.

Referring to FIGS. 2A and 2B, the ultrasound imaging apparatus 100a or 100b may include a main display 121 and a sub-display 122. At least one of the main display 121 and the sub-display 122 may include a touch screen. The main display 121 and the sub-display 122 may display ultrasound images and/or various information processed by the ultrasound imaging apparatus 100a or 100b. The main display 121 and the sub-display 122 may provide graphical user interfaces (GUI), thereby receiving user's inputs of data to control the ultrasound imaging apparatus 100a or 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound imaging apparatus 100a or 100b may control the display of the ultrasound image on the main display 121 by using the input control data.

Referring to FIG. 2B, the ultrasound imaging apparatus 100b may include a control panel 165. The control panel 165 may include buttons, trackballs, jog switches, or knobs, and may receive data to control the ultrasound imaging apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound imaging apparatus 100b may keep displaying a frame image at that time point.

The buttons, trackballs, jog switches, and knobs included in the control panel 165 may be provided as a GUI to the main display 121 or the sub-display 122.

Referring to FIG. 2C, an ultrasound imaging apparatus 100c may include a portable device. An example of a portable ultrasound imaging apparatus may include, for example, smart phones including probes and applications, laptop computers, personal digital assistants (PDAs), or tablet PCs, but an exemplary embodiment is not limited thereto.

The ultrasound imaging apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound imaging apparatus 100c, and a GUI.

A concept of a method of operating an ultrasound imaging apparatus will now be described in detail with reference to FIG. 3.

Figure 3:
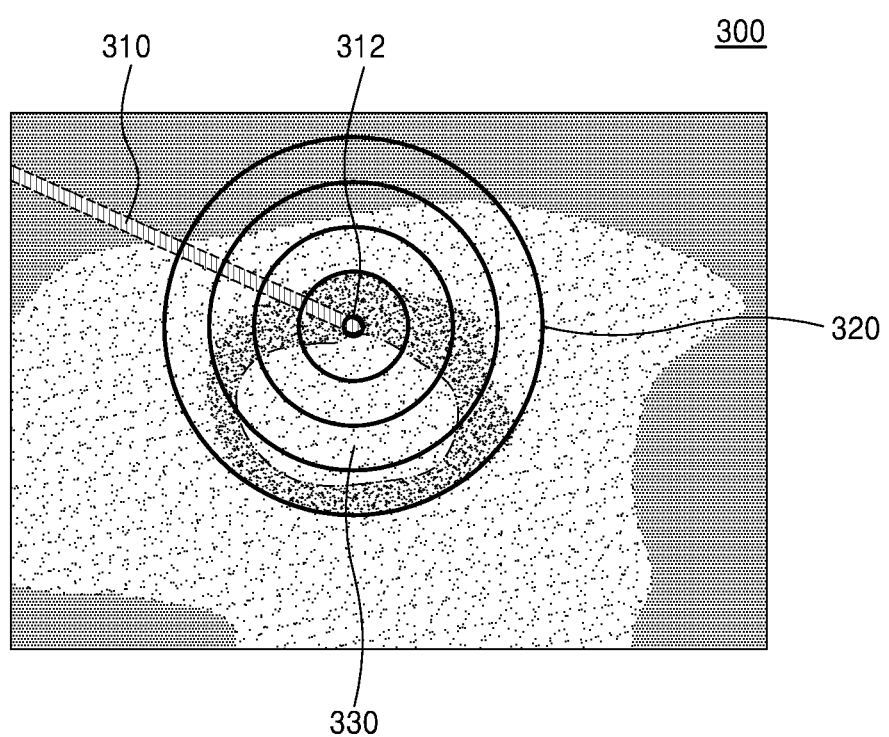
FIG. 3 is a diagram for explaining a method, performed by the ultrasound imaging apparatus, of displaying at least one distance-indicating line, according to an embodiment of the disclosure.

FIG. 3 is a diagram for explaining a method, performed by an ultrasound imaging apparatus, of displaying at least one distance-indicating line, according to an embodiment of the disclosure.

FIG. 3 shows an ultrasound image 300 displayed by the ultrasound imaging apparatus according to an embodiment of the disclosure. A medical tool 310 inserted into an object and a region of interest (ROI) 330 of the object are depicted in the ultrasound image 300.

According to an embodiment of the disclosure, the ultrasound imaging apparatus may detect a reference region 312 of the medical tool 310 in the ultrasound image 300, display at least one distance-indicating line 320 arranged around the reference region 312 in the ultrasound image 300, and update a position of the at least one distance-indicating line 320 according to movement of the medical tool 310. For example, as shown in FIG. 3, the ultrasound imaging apparatus may determine a distal end of the medical tool 310 as the reference region 312 and display the at least one distance-indicating line 320 with respect to the reference region 312. While FIG. 3 illustrates an example in which the number of distance-indicating lines 320 excluding a circle with the reference region 312 indicated therein is four (4), the ultrasound imaging apparatus may display one or more distance-indicating lines 320. The number of distance-indicating lines 320 may be determined automatically or by a user input.

When a user performs a medical activity of inserting the medical tool 310 into the object, the ultrasound imaging apparatus needs to display a scale or a guide for guiding the medical tool 310 in the ultrasound image 300 to allow the user to easily control the medical tool 310. For example, while performing a medical activity, the user may frequently perform caliper measurements by using the ultrasound imaging apparatus. The ultrasound imaging apparatus may assist the user in controlling the medical tool 310 by using a method of displaying a grid fixed regardless of real-time movement of the medical tool 310 across the entire ultrasound image 300. However, according to this method, the user has to temporarily suspend a medical activity in order to perform a caliper measurement during the medical activity. Furthermore, because the grid is fixedly displayed in the ultrasound image 300, the user has difficulties in identifying a relation between the medical tool 310 and the surrounding tissue when the medical tool 310 moves over the object.

According to various embodiments of the disclosure, the ultrasound imaging apparatus may display, with respect to the medical tool 310, at least one distance-indicating line whose position is updated according to movement of the medical tool 310 across the ultrasound image 300. Thus, when performing a medical activity of inserting the medical tool 310 into the object, the user may move the medical tool 310 without suspending the medical activity and easily identify a distance between the medical tool 310 and the surrounding tissue in real-time.

Figure 4:
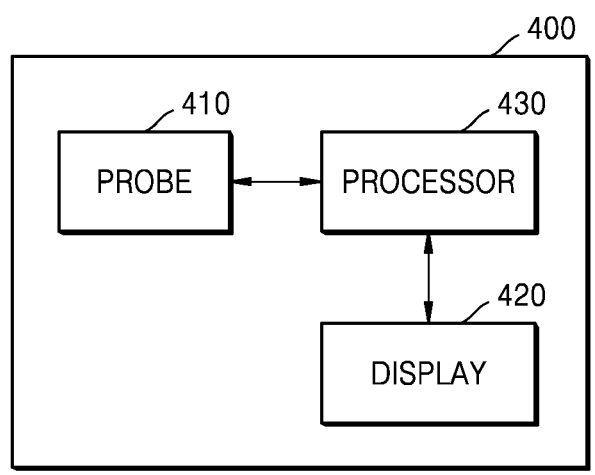
FIG. 4 illustrates a structure of an ultrasound imaging apparatus according to an embodiment of the disclosure.

FIG. 4 illustrates a structure of an ultrasound imaging apparatus 400 according to an embodiment of the disclosure.

According to an embodiment of the disclosure, the ultrasound imaging apparatus 400 may include a probe 410, a display 420, and a processor 430.

The ultrasound imaging apparatus 400 may be implemented in the form of an ultrasound imaging system, a general-purpose computer, a portable terminal, or a kiosk. For example, the ultrasound imaging system may be implemented as the ultrasound imaging apparatus 100 of FIG. 1, the ultrasound imaging apparatus 100a of FIG. 2A, the ultrasound imaging apparatus 100b of FIG. 2B, or the ultrasound imaging apparatus 100c of FIG. 2C.

The probe 410 may acquire ultrasound image data for generating an ultrasound image of an object. For example, the probe 410 may transmit ultrasound signals to the object and receive echo signals corresponding to the transmitted ultrasound signals. The received echo signals may be used to generate an ultrasound image of the object as data for generating an ultrasound image of the object. According to an embodiment of the disclosure, the probe 410 may correspond to the probe 20 of FIG. 1.

The display 420 may display an ultrasound image of the object. According to an embodiment of the disclosure, the display 420 may correspond to the display 140 of FIG. 1.

The processor 430 may control all operations of the ultrasound imaging apparatus 400 and process data. The processor 430 may include one or more processors. According to an embodiment of the disclosure, the processor 430 may be formed as a single processor or a plurality of processors for controlling the probe 410 and performing an operation of processing ultrasound signals. According to an embodiment of the disclosure, the processor 430 may correspond to the image processor 130 or a combination of the image processor 130 and the controller 120 described with reference to FIG. 1.

According to an embodiment of the disclosure, the ultrasound imaging apparatus 400 may provide a UI that allows the user to control the ultrasound imaging apparatus 400. The UI may be provided in various forms. For example, the ultrasound imaging apparatus 400 may include the sub-display 122 of FIG. 2A or 2B, and the UI may be provided as a control panel displayed by the sub-display 122 as a GUI. Furthermore, the ultrasound imaging apparatus 400 may include the control panel 165 of FIG. 2B, and the UI may be provided by buttons, trackballs, jog switches, knobs, etc. in the control panel 165. Furthermore, the display 420 of the ultrasound imaging apparatus 400 may be combined with a touch panel to form a touch screen, and the UI may be provided via a GUI displayed on the display 420.

According to an embodiment of the disclosure, the processor 430 may detect a reference region of a medical tool inserted into the object in an ultrasound image generated based on the echo signals, display at least one distance-indicating line arranged with respect to the reference region in the ultrasound image, and update a position of the at least one distance-indicating line according to movement of the medical tool.

According to an embodiment of the disclosure, the processor 430 may display on the display 420 the at least one distance-indicating line at set intervals with respect to the reference region of the medical tool. An interval between the at least one distance-indicating line may be automatically set by the ultrasound imaging apparatus 400 or may be set by a user input. According to an embodiment of the disclosure, an interval between the at least one distance-indicating line may be set based on the number of the at least one distance-indicating line. According to an embodiment of the disclosure, the number of the at least one distance-indicating line may be set based on an interval between the at least one distance-indicating line.

According to an embodiment of the disclosure, the processor 430 may control the display 420 to display information about a distance from the reference region of the medical tool to each of the at least one distance-indicating line.

According to an embodiment of the disclosure, the reference region of the medical tool may be at least a portion of the medical tool including a region where a distal end of the medical tool is located, and the processor 430 may control the display 420 to display the at least one distance-indicating line according to its distance from a border or center of the reference region.

According to an embodiment of the disclosure, the processor 430 may control the display 420 to visually display a reference region of the medical tool and fixedly display, in response to reception of an input of fixing a distance-indicating line, at least one distance-indicating line currently being displayed, regardless of movement of the medical tool.

According to an embodiment of the disclosure, the processor 430 may control the display 420 to visually display a reference region of a medical tool and hide currently displayed at least one distance-indicating line in response to reception of an input of hiding a distance-indicating line.

According to an embodiment of the disclosure, the processor 430 may provide a UI for setting at least one condition from among conditions for respectively setting the number and shape of at least one distance-indicating line, an interval between the at least one distance-indicating line, and a reference region of a medical tool.

According to an embodiment of the disclosure, a condition for setting a reference region of a medical tool may include at least one among a width, an area, and a shape of the reference region, and whether to set the reference region as a dot.

According to an embodiment of the disclosure, the shape of at least one distance-indicating line may include at least one from among a color, a transparency, and a pattern of the at least one distance-indicating line, and a transparency with respect to a distance of each of the at least one distance-indicating line from a reference region of a medical tool.

According to an embodiment of the disclosure, the processor 430 may control the display 420 to display at least one distance-indicating line arranged with respect to a preset region in an ultrasound image.

According to an embodiment of the disclosure, the processor 430 may control the display 420 to visually display at least one ROI in an ultrasound image and display information about a distance from a reference region of a medical tool to each of the at least one ROI.

According to an embodiment of the disclosure, the processor 430 may control the display 420 to display an extension line extending a long axis of a medical tool and at least one of a line connecting a distal end of the medical tool to at least one ROI, information about a distance between the distal end of the medical tool and the at least one ROI, and information about a shortest distance between the extension line and the at least one ROI.

A detailed example of a method of operating the ultrasound imaging apparatus 400 will be described below with reference to FIGS. 5 through 14.

Figure 5:
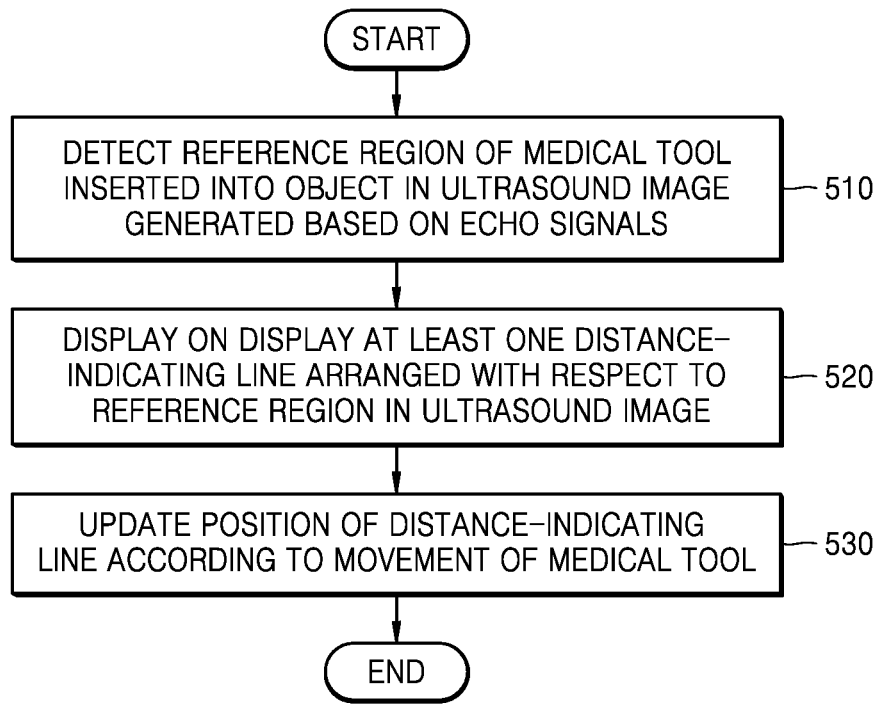
FIG. 5 is a flowchart of a method, performed by an ultrasound imaging apparatus, of displaying at least one distance-indicating line, according to an embodiment of the disclosure.

FIG. 5 is a flowchart of a method, performed by an ultrasound imaging apparatus, of displaying at least one distance-indicating line, according to an embodiment of the disclosure.

The ultrasound imaging apparatus 400 may detect a reference region of a medical tool that is inserted into an object in an ultrasound image generated based on echo signals received via the probe 410 (operation 510).

According to an embodiment of the disclosure, the ultrasound imaging apparatus 400 may detect a medical tool inserted into an object in an ultrasound image. In other words, the ultrasound imaging apparatus 400 may detect in real-time a position and a region where the medical tool is displayed in the ultrasound image. For example, the ultrasound imaging apparatus 400 may detect a medical tool by performing analysis of an ultrasound image generated based on echo signals received via the probe 410.

Furthermore, the ultrasound imaging apparatus 400 may detect a medical tool by using a technique for detecting an object by using an electromagnetic field. For example, an electromagnetic field generator may be located adjacent to the medical tool and create an electromagnetic field in a predetermined range of a region. The electromagnetic field generator may create a three-dimensional (3D) coordinate system in a region where the object and the medical tool are located. The medical tool may include an electromagnetic sensor for detecting an electromagnetic field. The ultrasound imaging apparatus 400 may include a tracker for acquiring information about a position of the medical tool and its movement direction. The electromagnetic sensor of the medical sensor may detect an electromagnetic field created by the electromagnetic field generator and provide the tracker with information about a position of the medical tool, which is detected in a 3D space. The ultrasound imaging apparatus 400 may detect the medical tool inserted into the object in an ultrasound image generated based on echo signals received via the probe 410, based on information about the position of the medical tool and its movement direction, which is acquired by the tracker.

In addition, a method, performed by the ultrasound imaging apparatus 400, of detecting a medical tool in an ultrasound image is not limited the above-described examples, and various other methods may be used to detect a medical tool in an ultrasound image.

The ultrasound imaging apparatus 400 may detect a reference region of the detected medical tool.

The reference region of the medical tool is a region used as a reference for displaying at least one distance-indicating line in the ultrasound image. The reference region of the medical tool may be at least a portion of a region where the medical tool is displayed in the ultrasound image.

According to an embodiment of the disclosure, the reference region of the medical tool may be a distal end of the medical tool or at least a portion of the medical tool including a region where the distal end of the medical tool is located. For example, when the medical tool is a medical needle, the reference region of the medical tool may be a needle tip or at least a portion of the needle including the needle tip.

According to an embodiment of the disclosure, a reference region of the medical tool may be set by the user. For example, the user may set a condition for setting a reference region of the medical tool via a UI provided by the ultrasound imaging apparatus 400. The condition for setting the reference region of the medical tool may include at least one from among a width, an area, and a shape of the reference region, and whether to set the reference region as a dot. In other words, the user may set at least a portion of a region where the medical tool is displayed in an ultrasound image as the reference region.

According to an embodiment of the disclosure, the ultrasound imaging apparatus 400 may detect only the reference region of the medical tool inserted into the object in the ultrasound image instead of detecting the entire medical tool therein.

The ultrasound imaging apparatus 400 may control the display 420 to display at least one distance-indicating line arranged with respect to the reference region in the ultrasound image (operation 520).

At least one distance-indicating line means at least one indicating line arranged with respect to the reference region such that a position of the medical tool with respect to tissues of the object surrounding the medical tool may be easily identified.

The number and shape of at least one distance-indicating line, an interval between the at least one distance-indicating line, etc. may be determined in various ways. For example, the at least one distance-indicating line may be displayed as at least one circle having a center of the reference region as its center.

Furthermore, the at least one distance-indicating line may be displayed in a shape corresponding to that of the reference region. For example, when the reference region is of a round rectangular shape with round corners, each of the at least one distance-indicating line may be displayed as a round rectangle with a center of the reference region as its center and round corners.

According to an embodiment of the disclosure, the ultrasound imaging apparatus 400 may visually display a region where the medical tool is located or the reference region of the medical tool. For example, the ultrasound imaging apparatus 400 may display a border of the region where the medical tool is located or a border of the reference region of the medical tool. The ultrasound imaging apparatus 400 may display a border of the region where the medical tool is located or the reference region, thereby allowing easy identification of a position and movement of the medical tool as well as a region used as a reference for displaying distance information regarding at least one distance line.

Various types of the at least one distance-indicating line will be described in more detail below with reference to FIGS. 6 through 8.

According to an embodiment of the disclosure, the ultrasound imaging apparatus 400 may display distance information about a distance from the reference region of the medical tool to each of the at least one distance-indicating line. By displaying the above-described distance information, the ultrasound imaging apparatus 400 may quantitatively identify a position of the medical tool with respect to tissues surrounding the medical tool.

According to an embodiment of the disclosure, a condition for displaying at least one distance-indicating line may be set by the user. For example, the user may set a condition for displaying at least one distance-indicating line via a UI provided by the ultrasound imaging apparatus 400. The condition for displaying at least one distance-indicating line may include at least one from among the number and shape of the at least one distance-indicating line and an interval between the at least one distance-indicating line.

For example, the shape of the at least one distance-indicating line may include at least one from among a color, a transparency, and a pattern of the at least one distance-indicating line, and a transparency with respect to a distance of each of the at least one distance-indicating line from the reference region of the medical tool.

Furthermore, according to an embodiment of the disclosure, the ultrasound imaging apparatus 400 may display in an ultrasound image at least one distance-indicating line arranged with respect to a preset region other than the reference region of the medical tool. The preset region may be set by the user via a UI provided by the ultrasound imaging apparatus 400. For example, the preset region may be any of various ROIs such as tissues, lesions, etc., in the object.

By displaying the at least one distance-indicating line arranged with respect to the preset region, the ultrasound imaging apparatus 400 may visually display a relative position of the medical tool with respect to the preset region.

Various types of the at least one distance-indicating line arranged with respect to the preset region and methods of displaying the at least one distance-indicating line may respectively correspond to various types of at least one distance-indicating line arranged with respect to the reference region of the medical tool and methods of displaying the at least one distance-indicating line.

The ultrasound imaging apparatus 400 may update a position of the at least one distance-indicating line according to movement of the medical tool (operation 530).

As the user manipulates the medical tool, the position of the medical tool moves over the ultrasound image. As described with reference to operation 520, the ultrasound imaging apparatus 400 may detect in real-time a position and a region where the medical tool or the reference region of the medical tool is displayed in the ultrasound image.

As the position of the reference region of the medical tool changes in the ultrasound image due to movement of the medical tool, the ultrasound imaging apparatus 400 may display at least one distance-indicating line with respect to the reference region having the changed position. In other words, the ultrasound imaging apparatus 400 may update a position of the at least one distance-indicating line according to movement of the medical tool.

The ultrasound imaging apparatus 400 may update the position of the at least one distance-indicating line as the medical tool moves, thereby allowing the user to move, when performing a medical activity of inserting the medical tool into the object, the medical tool without suspending the medical activity and easily identify a distance between the medical tool and the surrounding tissue in real-time.

Figure 6:
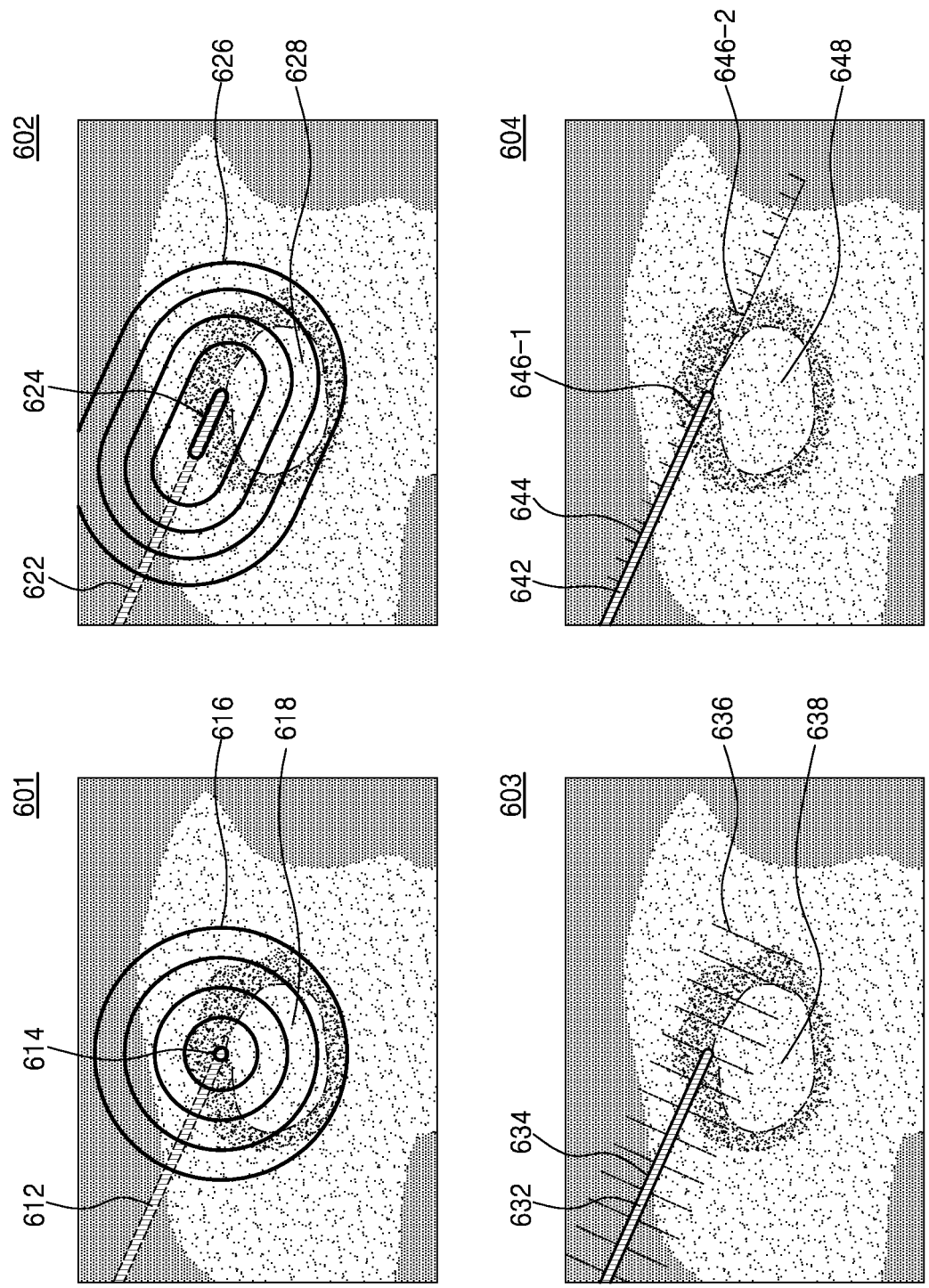
FIG. 6 is a diagram for explaining various shapes of distance-indicating lines that can be displayed by an ultrasound imaging apparatus, according to an embodiment of the disclosure.

FIG. 6 is a diagram for explaining various shapes of distance-indicating lines that can be displayed by the ultrasound imaging apparatus 400, according to an embodiment of the disclosure As described with reference to operation 520 of FIG. 5, the number and shape of at least one distance-indicating line, an interval between the at least one distance-indicating line, etc. may be determined in various ways. Furthermore, a border of a region where a medical tool is located or a border of a reference region of the medical tool may be displayed.

Referring to 601 of FIG. 6, for example, at least one distance-indicating line 616 may be displayed as at least one circle, each having a center of a reference region 614 as its center, wherein a distal end of a medical tool 612 is determined as the reference region 614.

601 of FIG. 6 shows an example in which the number of at least one distance-indicating line 616 excluding a circle with the reference region 614 indicated therein is four (4). The at least one distance-indicating line 616 may be displayed according to its distance from a border or center of the reference region 614.

The at least one distance-indicating line 616 may be displayed at regular intervals from the border of the reference region 614. For example, when the reference region 614 is a circle with a radius r and an interval between the at least one distance-indicating line 616 is L, the at least one distance-indicating line 616 may be four circles respectively having radii of r+L, r+2L, r+3L, and r+4L.

Furthermore, unlike in 601 of FIG. 6, the reference region 614 of the medical tool 612 may not be displayed as a circle and may be depicted in various ways, e.g., by displaying the center of the reference region 614 as a dot. Alternatively, the reference region 614 may not be displayed.

Furthermore, the at least one distance-indicating line 616 may be displayed as at least one circle at regular intervals, each circle having the center of the reference region 614 as its center. For example, when an interval between the at least one distance-indicating line 616 is L, the at least one distance-indicating line 616 may be four circles respectively having radii of L, 2L, 3L, and 4L.

Furthermore, the number of the at least one distance-indicating line 616 is not limited to the example shown in 601 of FIG. 6 but may be determined in various other ways.

The ultrasound imaging apparatus 400 may display the at least one distance-indicating line 616 circularly around the reference region 614 as shown in 601 of FIG. 6, thereby allowing easy identification of a position or distance of the reference region 614 of the medical tool 612 relative to tissue and an ROI 618 of the object. For example, a distance from the distal end of the medical tool 612 to the tissue or ROI 618 of the object may be visually identified.

Referring to 602 of FIG. 6, for example, each of at least one distance-indicating line 626 may be displayed as a round rectangle having a center of a reference region 624 as its center and round corners, wherein the reference region 624 is at least a portion of a medical tool 622 including a region where a distal end of the medical tool 622 is located.

602 of FIG. 6 shows an example in which the number of at least one distance-indicating line 626 excluding one with the reference region 624 indicated therein is four (4). The at least one distance-indicating line 626 may be displayed according to its distance from a border or center of the reference region 624.

The at least one distance-indicating line 626 may be displayed at regular intervals from a border of the reference region 624. For example, when an interval between the at least one distance-indicating line 626 is L, the at least one distance-indicating line 626 may be respectively displayed with intervals of L, 2L, 3L, and 4L away from the reference region 624.

Furthermore, unlike in 602 of FIG. 6, the reference region 624 of the medical tool 622 may not be displayed as a round rectangle and may be depicted in various other shapes, e.g., by displaying the center of the reference region 624 as a dot. Alternatively, the reference region 624 may not be displayed. The at least one distance-indicating line 626 may be displayed as at least one round rectangle with round corners at regular intervals, each round rectangle having the center of the reference region 624 as its center.

Furthermore, the number of the at least one distance-indicating line 626 is not limited to the example shown in 602 of FIG. 6 but may be determined in various other ways.

Referring to 601 and 602 of FIG. 6, the at least one distance-indicating line (616 or 626) may be displayed in a shape corresponding to that of the reference region 614 or 624 of the medical tool (612 or 622). For example, when the reference region 614 of the medical tool 612 has a circular shape as shown in 601 of FIG. 6, the at least one distance-indicating line 616 may also be displayed as at least one circle. When the reference region 624 of the medical tool 622 has a round rectangular shape as shown in 602 of FIG. 6, the at least one distance-indicating line 626 may also be displayed as at least one round rectangle with round corners. A shape of a reference region of a medical tool and a method of displaying at least one distance-indicating line in a shape corresponding to that of the reference region are not limited to the above-described examples but may be determined in various other ways.

The ultrasound imaging apparatus 400 may display the at least one distance-indicating line 626 as at least one rectangle with round corners at specific intervals from the reference region 624 as shown in 602 of FIG. 6, thereby allowing easy identification of a position or distance of the reference region 624 of the medical tool 622 relative to tissue and an ROI 628 of the object. For example, a distance from at least a portion of the medical tool 622 including a distal end of the medical tool 622 to the tissue or ROI 628 of the object may be visually identified.

Referring to 603 of FIG. 6, for example, at least one distance-indicating line 636 may be at least one line perpendicular to a long axis of a medical tool 632.

Referring to 603 of FIG. 6, a region where the medical tool 632 is located is determined as a reference region 634 of the medical tool 632, and a border of the reference region 634 is displayed.

603 of FIG. 6 shows an example in which the number of the at least one distance-indicating line 636 excluding one with the reference region 634 indicated therein is thirteen (13). The at least one distance-indicating line 636 is perpendicular to the long axis of the medical tool 632, and thus, is shown as being perpendicular to a long line of the border of the reference region 634.

The at least one distance-indicating line 636 may be displayed at regular intervals across the reference region 634. Furthermore, the at least one distance-indicating line 636 may not cross the reference region 634 but may be displayed in front of a distal end of the medical tool 632. 603 of FIG. 6 shows an example in which nine (9) lines of the at least one distance-indicating line 636 cross the reference region 634 while four (4) lines do not cross the same.

Each of the at least one distance-indicating line 636 may be a line of the same length. However, the type of the at least one distance-indicating line 636 shown as being perpendicular to the long axis of the medical tool 632 is not limited to the example shown in 603 of FIG. 6 but may be determined in various ways. For example, the number of the at least one distance-indicating line 636, the number of distance-indicating lines displayed before the distal end of the medical tool 632, an interval between the at least one distance-indicating line 636, etc. may be determined in various ways.

Furthermore, each of the at least one distance-indicating line 636 may have a different length, and the at least one distance-indicating line 636 may have irregular intervals therebetween. For example, as a distance from the distal end of the medical tool 632 increases, an interval between the at least one distance-indicating line 636 may decrease or increase.

Referring to 604 of FIG. 6, for example, at least one distance-indicating line may include a line 646-2 extending from a distal end of a medical tool 642 along (or parallel to) a long axis of the medical tool 642.

Referring to 604 of FIG. 6, a region where the medical tool 642 is located is determined as a reference region 644 of the medical tool 642, and a border of the reference region 644 is displayed.

The line 646-2 extending from the distal end of the medical tool 642 may visually indicate a region where the distal end of the medical tool 642 is to be positioned when the medical tool 642 moves linearly in a direction that the long axis of the medical tool 642 is currently oriented.

The line 646-2 extending from the distal end of the medical tool 642 may include at least one scale mark perpendicular to the line 646-2. The at least one scale mark may be displayed at regular intervals.

Furthermore, the at least one distance-indicating line may include at least one scale mark 646-1 on the border of the reference region 644 of the medical tool 642. The at least one scale mark 646-1 may be displayed on or parallel to a long line of the border of the reference region 644 at regular intervals.

The ultrasound imaging apparatus 400 may display at least one distance-indicating line in various shapes as shown in 601 through 604 of FIG. 6, thereby allowing visual identification of a position or distance of a reference region of a medical tool relative to tissue and ROIs 618, 628, 638, and 648 of the object according to various methods.

In addition, the shapes of at least one distance-indicating line are not limited to the examples shown in 601 through 604 of FIG. 6, but may be determined as various other shapes. For example, the at least one distance-indicating line may be displayed in a grid form, as described in more detail below with reference to FIG. 7.

Furthermore, the user may use a UI provided by the ultrasound imaging apparatus 400 to select one of various shapes of distance-indicating lines or set at least one from among the number and shape of at least one distance-indicating line, an interval between the at least one distance-indicating line, and a condition for setting a reference region of a medical tool. A condition for setting a reference region of a medical tool may include at least one from among a width, an area, and a shape of the reference region, and whether to set the reference region as a dot.

The shape of at least one distance-indicating line may include at least one from among a color, a transparency, and a pattern of the at least one distance-indicating line, and a transparency with respect to a distance of each of the at least one distance-indicating line from a reference region of a medical tool. For example, the user may use a UI to set the ultrasound imaging apparatus 400 to display at least one distance-indicating line as a solid line pattern or dashed line pattern and set a transparency of the at least one distance-indicating line to increase or decrease as a distance from a reference region of a medical tool increases. Characteristics that may be set by the user with respect to at least one distance-indicating line via a UI is not limited to the above-described examples, and may be determined in various ways.

Figure 7:
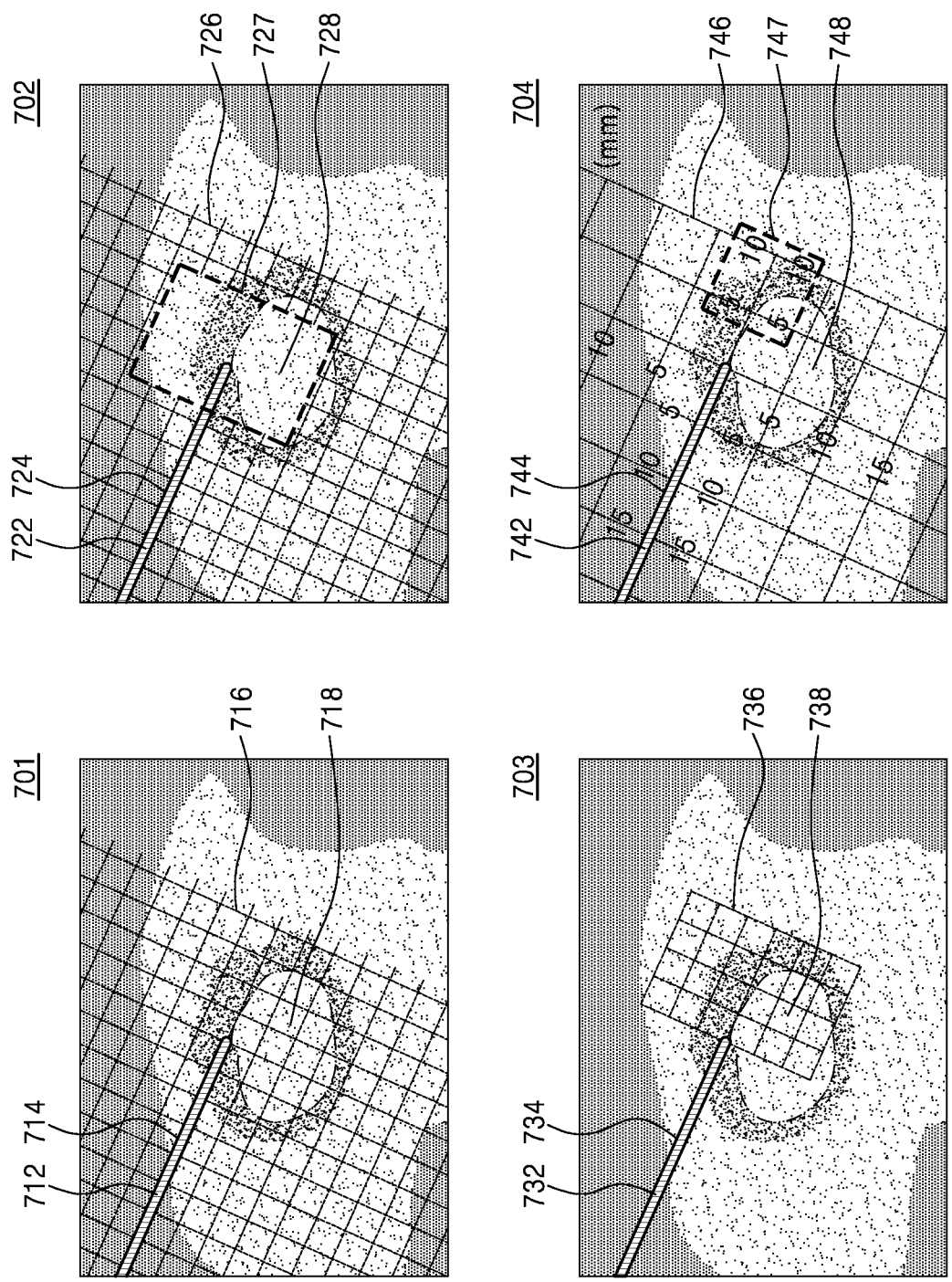
FIG. 7 is a diagram for explaining various shapes of grid-type distance-indicating lines that can be displayed by an ultrasound imaging apparatus, according to an embodiment of the disclosure.

FIG. 7 is a diagram for explaining various shapes of grid-type distance-indicating lines that can be displayed by the ultrasound imaging apparatus 400, according to an embodiment of the disclosure.

FIG. 7 shows an example in which regions where medical tools 712, 722, 732, and 742 are located are respectively determined as reference regions 714, 724, 734, and 744 of the medical tools 712, 722, 732, and 742, and borders of the reference regions 714, 724, 734, and 744 and ROIs 718, 728, 738, and 748 are displayed.

Referring to 701 of FIG. 7, according to an embodiment of the disclosure, the ultrasound imaging apparatus 400 may display a grid-type distance-indicating line 716 with respect to the reference region 714 of the medical tool 712.

An interval of the grid-type distance-indicating line 716, the number of horizontal and vertical lines in the grid-type distance-indicating line 716, and a distance from the reference region 714 to a point up to which the grid-type distance-indicating line 716 is displayed, etc., may be determined in various ways. For example, as shown in 701 of FIG. 7, the ultrasound imaging apparatus 400 may display, in front of a distal end of the medical tool 712, horizontal or vertical lines of the grid-type distance-indicating line 716 up to only a point that is at a preset distance away from the distal end of the medical tool 712.

By displaying a grid-type distance-indicating line 716 in only a portion of an ultrasound image with respect to the medical tool 712, as shown in 701 of FIG. 7, the ultrasound imaging apparatus 400 may clearly display the rest of the ultrasound image where the grid-type distance-indicating line 716 is not displayed and simultaneously provide visual information about a distance relation between the medical tool 712 and its surroundings.

As described with reference to operation 530 of FIG. 5, as the position of the reference region 714 of the medical tool 712 changes in the ultrasound image due to movement of the medical tool 712, the ultrasound imaging apparatus 400 may display the grid-type distance-indicating line 716 with respect to the reference region 714 having the changed position. By updating a position of the grid-type distance-indicating line 716 with respect to the reference region 714 according to the movement of the medical tool 712, the ultrasound imaging apparatus 400 may provide in real-time visual information about a distance relation between the medical tool 712 and either the surrounding tissue or an ROI.

Various types of grid-type distance-indicating lines will now be described in more detail with reference to 702 of FIG. 7 through 704 of FIG. 7.

Referring to 702 of FIG. 7, for example, a grid-type distance-indicating line 726 may include a first region 727 where grid lines are not displayed. In other words, the grid-type distance-indicating line 726 shown in 702 of FIG. 7 is different from the grid-type distance-indicating line 716 shown in 701 of FIG. 7 in that grid lines are not only displayed in the first region 727.

The first region 727 may be a region centered around a distal end of the medical tool 722. Furthermore, as shown in 702 of FIG. 7, a line extending from the distal end of the medical tool 722 along (or parallel to) a long axis of the medical tool 722 may be displayed in the first region 727 of the grid-type distance-indicating line 726.

The ultrasound imaging apparatus 400 may display, with respect to a distal end of the medical tool 722, the grid-type distance-indicating line 726 including the first region 727 where grid lines are not displayed, as shown in 702 of FIG. 7, thereby clearly displaying a region surrounding the distal end of the medical tool 722 in an ultrasound image and simultaneously providing visual information about a distance relation between the medical tool 722 and its surroundings. For example, grid lines may not be displayed in the first region 727 such that an ROI 728 surrounding the distal end of the medical tool 722 may be clearly visible.

Referring to 703 of FIG. 7, a grid-type distance-indicating line 736 may be only displayed in a portion of surroundings of the medical tool 732.

As shown in 703 of FIG. 7, by displaying the grid-type distance-indicating line 736 only in a portion of a region surrounding the distal end of the medical tool 732, the ultrasound imaging apparatus 400 may intensively provide visual information about a distance relation between the distal end of the medical tool 732 and its surrounding area.

Referring to 704 of FIG. 7, for example, the ultrasound imaging apparatus 400 may display information about a distance from a distal end of the medical tool 742 to each of the grid lines in a grid-type distance-indicating line 746. The grid-type distance-indicating line 746 shown in 704 of FIG. 7 may be obtained by adjusting the interval of the grid-type distance-indicating line 716 shown in 701 of FIG. 7.

Referring to 704 of FIG. 7, shortest distance information is displayed for grid lines respectively having shortest distances of 5 millimeters (mm), 10 mm, and 15 mm from the distal end of the medical tool 742. As shown in 747 of FIG. 7, pieces of distance information respectively regarding grid lines arranged in front of the distal end of the medical tool 742 are indicated as '5' and '10', and the mm that is a unit of distance is displayed at the top right corner of an ultrasound image.

A method, performed by the ultrasound imaging apparatus 400, of displaying distance information regarding each of the grid lines in the grid-type distance-indicating line 746 is not limited to the example shown in 704 of FIG. 7. For example, although 704 of FIG. 7 shows an example in which only a piece of distance information is displayed for each grid line, a plurality of pieces of distance information may be displayed for each grid line. Furthermore, distance information about a distance from the reference region 744 of the medical tool 742 may be displayed. The distance information may be displayed together with a unit of distance, and the unit of distance is not limited to mm but may be determined as various other distance units such as a centimeter (cm).

In addition, the shape of a grid-type distance-indicating line is not limited to the examples shown in 701 through 704 of FIG. 7, and may be determined as various other shapes. For example, the number of grid lines in a grid-type distance-indicating line, an interval between grid lines, a color of each grid line, etc. may be determined in various ways and may be set by a user via a UI provided by the ultrasound imaging apparatus 400.

Figure 8:
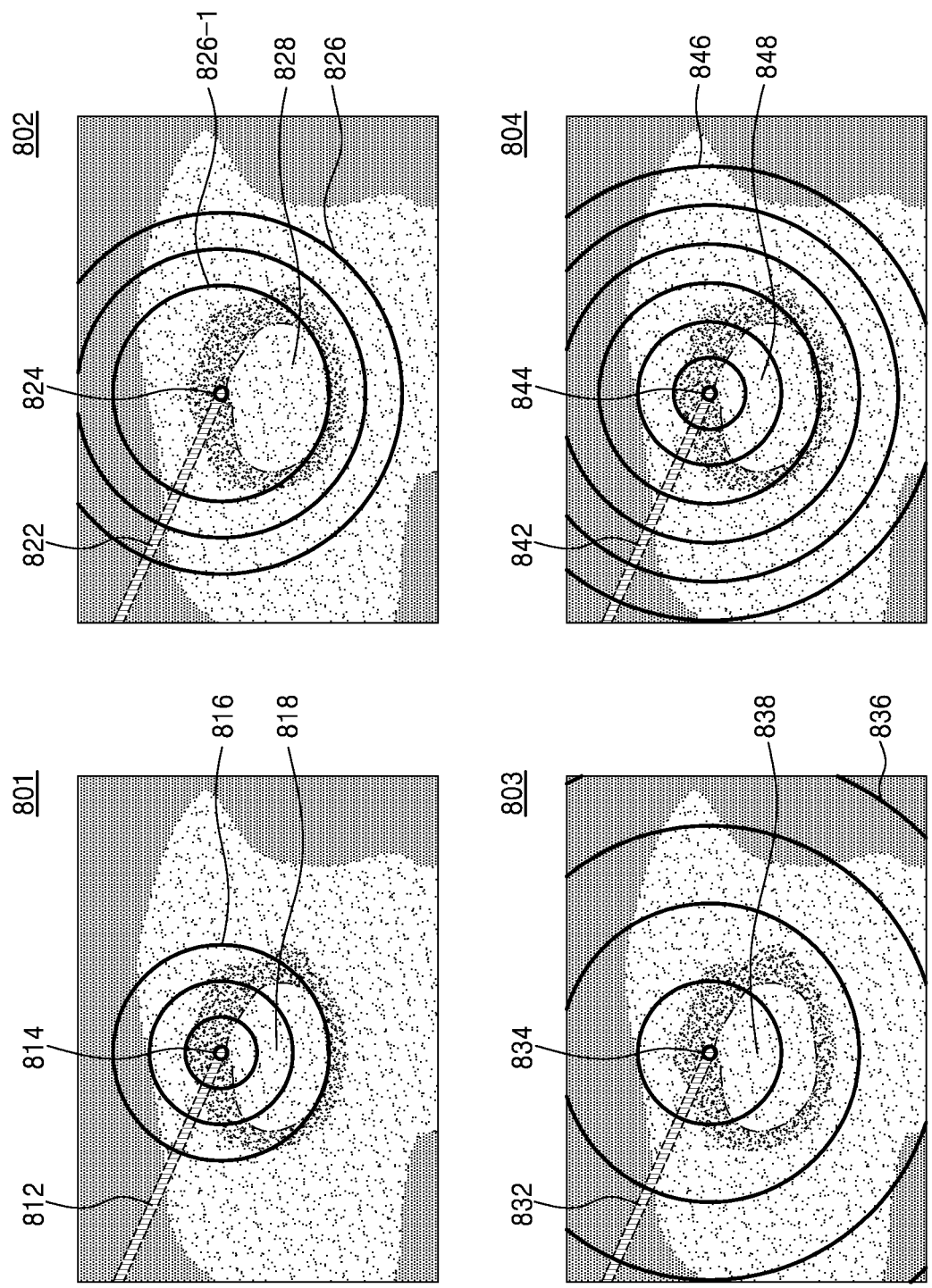
FIG. 8 is a diagram for explaining a method, performed by an ultrasound imaging apparatus, of displaying at least one distance-indicating line with respect to a medical tool, according to an embodiment of the disclosure.

FIG. 8 is a diagram for explaining a method, performed by the ultrasound imaging apparatus 400, of displaying at least one distance-indicating line with respect to a medical tool and ROIs 818, 828, 838, and 848, according to an embodiment of the disclosure.

According to an embodiment of the disclosure, the ultrasound imaging apparatus 400 may display at least one distance-indicating line at set intervals with respect to a reference region 814, 824, 834, and 844, of a medical tool 812, 822, 832, and 842.

A method, performed by the ultrasound imaging apparatus 400, of determining and displaying an interval between at least one distance-indicating line having a circular shape in various ways will now be described in detail with reference to FIG. 8. In other words, at least one distance-indicating lines 816, 826, 836, and 846 shown in FIG. 8 may be a modified form of the at least one distance-indicating line 616 shown in 601 of FIG. 6.

Referring to 801 of FIG. 8, at least one distance-indicating line 816 may be displayed as at least one circle, each having a center of the reference region 814 as its center, wherein a distal end of the medical tool 812 is determined as the reference region 814.

Referring to 802 of FIG. 8, at least one distance-indicating line 826 may include a first distance-indicating line 826-1 displayed at a first distance from the reference region 824, and an interval between the at least one distance-indicating line 826 may be a second distance different from the first distance.

For example, as shown in 802 of FIG. 8, the ultrasound imaging apparatus 400 may clearly display surroundings of the reference region 824 by not displaying a distance-indicating line up to a point that is at the first distance away from the reference region 824 of the medical tool 822 and simultaneously display the at least one distance-indicating line 826 behind the point that is at the first distance from the reference region 824.

Referring to 803 and 804 of FIG. 8, the number of and an interval between at least one distance-indicating line may be determined in various ways. 803 of FIG. 8 shows at least one distance-indicating line 836 having a wider interval therebetween than the at least one distance-indicating line 816 shown in 801 of FIG. 8. 804 of FIG. 8 shows at least one distance-indicating line 846 having a narrower interval therebetween than the at least one distance-indicating line 816 shown in 801 of FIG. 8. Furthermore, while the number of the at least one distance-indicating line 816 in 801 of FIG. 8 is three (3), the numbers of the at least one distance-indicating line 836 in 803 of FIG. 8 and the at least one distance-indicating line 846 in 804 of FIG. 8 are respectively four (4) and six (6).

In addition, a method of displaying at least one distance line by adjusting an interval therebetween is not limited to the examples shown in 801 through 804 of FIG. 8, and various other methods may be used. For example, an interval between each of the at least one distance-indicating line may be determined differently. As a distance from a reference region of a medical tool increases, an interval between the at least one distance-indicating line may decrease or increase. Furthermore, an interval between at least one distance-indicating line may be set by a user via a UI provided by the ultrasound imaging apparatus 400.

As described with reference to FIGS. 6 through 8, the ultrasound imaging apparatus 400 may display various types of at least one distance-indicating line.

Methods of operating the ultrasound imaging apparatus 400 when at least one distance-indicating line has a circular shape (e.g., the shape shown in 601 of FIG. 6) or a round rectangular shape with round corners (the shape shown in 602 of FIG. 6) will be described in more detail below. However, the methods of operating the ultrasound imaging apparatus 400 may also be applied even when the at least one distance-indicating line does not have a circular or round rectangular shape.

Figure 9A:
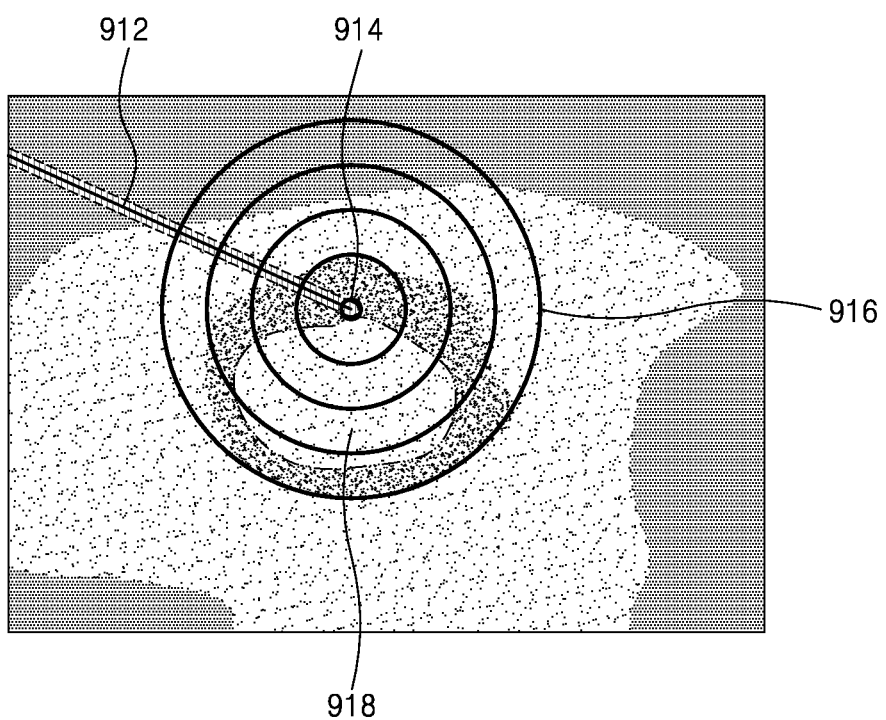
FIGS. 9A and 9B are diagrams for explaining a method, performed by an ultrasound imaging apparatus, of displaying at least one distance-indicating line with respect to a medical tool or a preset region, according to an embodiment of the disclosure.
Figure 9B:
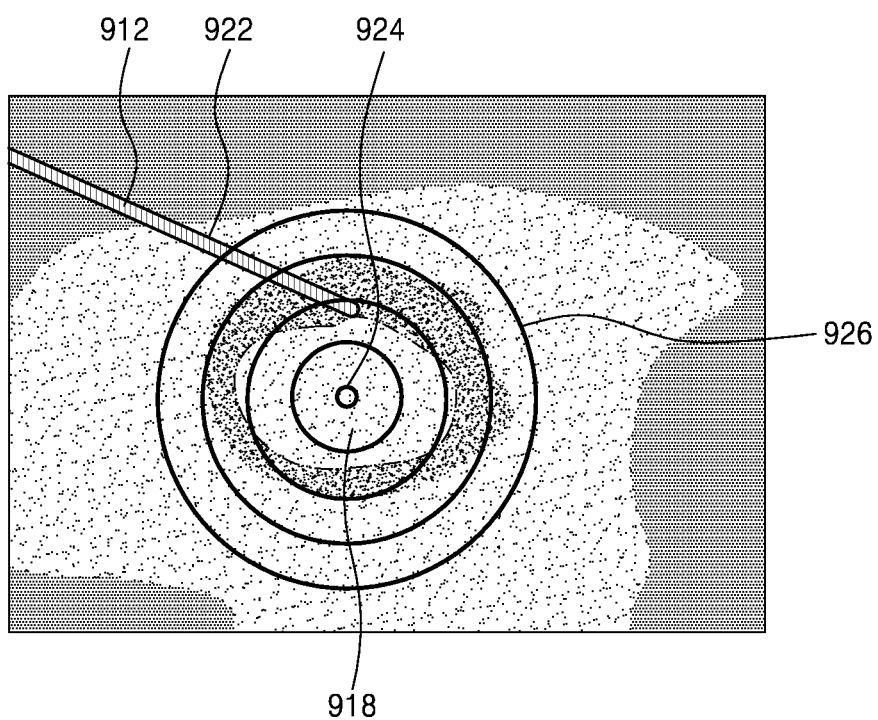

FIGS. 9A and 9B are diagrams for explaining a method, performed by the ultrasound imaging apparatus 400, of displaying at least one distance-indicating line with respect to a medical tool or a preset region, according to an embodiment of the disclosure.

Referring to FIG. 9A, the ultrasound imaging apparatus 400 may determine a distal end of a medical tool 912 as a reference region 914 and display at least one distance-indicating line 916 with a center of the reference region 914 as its center.

By displaying the at least one distance-indicating line 916 with respect to the reference region 914 of the medical tool 912, the ultrasound imaging apparatus 400 may allow the user to visually identify a position or distance of the reference region 914 of the medical tool 912 relative to tissue or an ROI 918 of an object with respect to the reference region 914 of the medical tool 912.

Referring to FIG. 9B, according to an embodiment of the disclosure, the ultrasound imaging apparatus 400 may display at least one distance-indicating line 926 arranged around a preset region 924.

The preset region 924 refers to a region of the object used as a reference in displaying the at least one distance-indicating line 926. The preset region 924 may be determined in various ways, and for example, may be at least a portion of the ROI 918 of the object.

According to an embodiment of the disclosure, the preset region 924 may be set by the user. For example, the user may set the preset region 924 within the object via a UI provided by the ultrasound imaging apparatus 400.

Various types of the at least one distance-indicating line 926 arranged with respect to the preset region 924 and methods of displaying the at least one distance-indicating line 926 may respectively correspond to various types of the at least one distance-indicating line 916 arranged with respect to the reference region 914 of the medical tool 912 and methods of displaying the at least one distance-indicating line 916.

Furthermore, when the at least one distance-indicating line 926 is displayed with respect to the preset region 924, the ultrasound imaging apparatus 400 may visually display a border 922 of the medical tool 912 such that the medical tool 912 may be easily identified in an ultrasound image.

By displaying the at least one distance-indicating line 926 with respect to the preset region 924, the ultrasound imaging apparatus 400 may allow the user to visually identify a position or distance of the medical tool 912 relative to tissue or the ROI 918 of the object with respect to the preset region 924.

Figure 10:
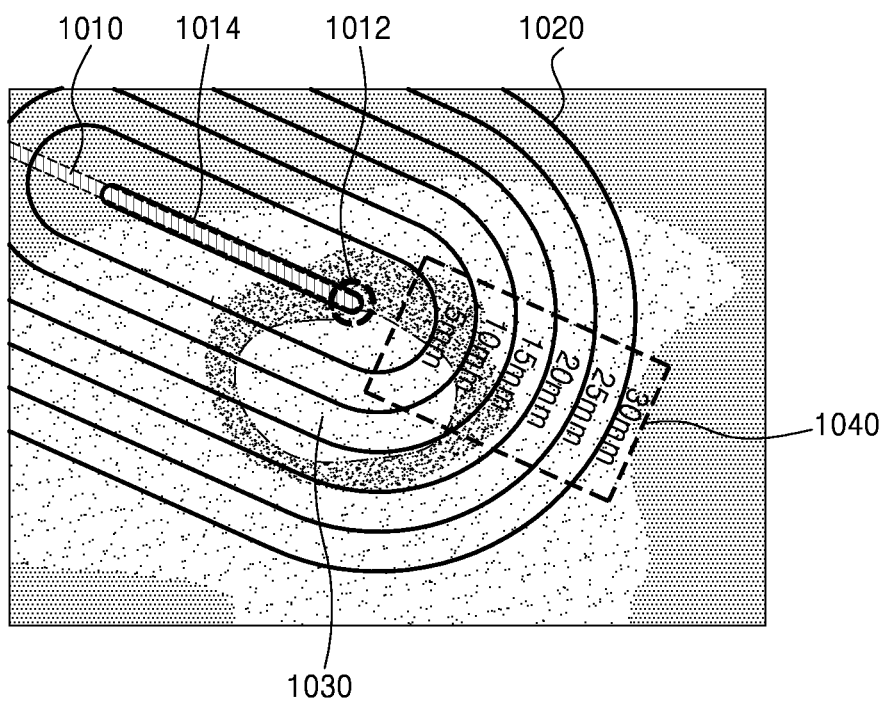
FIG. 10 is a diagram for explaining a method, performed by an ultrasound imaging apparatus, of displaying at least one distance-indicating line together with distance information by determining at least a portion of a medical tool as a reference region, according to an embodiment of the disclosure.

FIG. 10 is a diagram for explaining a method, performed by the ultrasound imaging apparatus 400, of displaying at least one distance-indicating line together with distance information by determining at least a portion of a medical tool as a reference region, according to an embodiment of the disclosure.

Referring to FIG. 10, as described with reference to 602 of FIG. 6, the ultrasound imaging apparatus 400 may determine a portion of a medical tool 1010 including a distal end 1012 of the medical tool 1010 as a reference region 1014 and display at least one distance-indicating line 1020 as at least one round rectangle with round corners with respect to the reference region 1014.

The ultrasound imaging apparatus 400 may display distance information 1040 about a distance from the reference region 1014 to each of the at least one distance-indicating line 1020.

For example, as shown in FIG. 10, the distance information 1040 about a distance from the reference region 1014 may be displayed for each of the at least one distance-indicating line 1020 arranged at 5 mm intervals away from the reference region 1014. mm that is the unit of distance may be displayed together with a numeral indicating a distance as shown in FIG. 10, or may be indicated on a portion of the ultrasound image as shown in 704 of FIG. 7.

A method of displaying the distance information 1040 in an ultrasound image is not limited to the example shown in FIG. 10. For example, although FIG. 10 shows that the distance information 1040 is displayed in front of the distal end 1012 of the medical tool 1010, the distance information 1040 may be displayed using various methods such as being indicated on a side of the medical tool 1010 or the at least one distance-indicating line 1020.

A method, performed by the ultrasound imaging apparatus 400, of respectively displaying distance information regarding the at least one distance-indicating line 1020 is not limited to the example shown in FIG. 10. For example, while FIG. 10 shows an example in which only a piece of distance information is displayed for each of the at least one distance-indicating line 1020, a plurality of pieces of distance information may be displayed for each of the at least one distance-indicating line 1020. Furthermore, the distance information may be displayed together with a unit of distance, and the unit of distance is not limited to mm but may be determined as various other distance units such as cm.

The ultrasound imaging apparatus 400 may display the distance information 1040 about a distance from the reference region 1014 for each of the at least one distance-indicating line 1020, such that a position of the medical tool 1010 with respect to tissue or an ROI 1030 surrounding the medical tool 1010 may be identified quantitatively.

FIG. 11 is a diagram for explaining operations of the ultrasound imaging apparatus 400 in a distance-indicating line fixed mode and in a distance-indicating line hidden mode, according to an embodiment of the disclosure.

According to an embodiment of the disclosure, the ultrasound imaging apparatus 400 may display at least one distance-indicating line by updating a position of the at least one distance-indicating line according movement of a medical tool with respect to an ROI 1130. An operation mode in which the ultrasound imaging apparatus 400 displays at least one distance-indicating line by updating a position of the at least one distance-indicating line according to movement of a medical tool is referred to as a 'first operation mode'.

In addition, according to an embodiment of the disclosure, the ultrasound imaging apparatus 400 may operate in a distance-indicating line fixed mode or in a distance-indicating line hidden mode.

A distance-indicating line fixed mode is an operation mode in which the ultrasound imaging apparatus 400 fixedly displays at least one distance-indicating line and displays a changed position of a medical tool in an ultrasound image at a predetermined time point or during a predetermined time period.

A distance-indicating line hidden mode is an operation mode in which the ultrasound imaging apparatus 400 display only a position of the medical tool while not displaying at least one distance-indicating line in an ultrasound image at a predetermined time point or during a predetermined time period.

While performing a medical activity, the user may select an operation mode of the ultrasound imaging apparatus 400 via a UI provided by the ultrasound imaging apparatus 400. For example, the user may select an operation mode by touching an icon for turning on/off a distance-indicating line fixed mode or distance-indicating line hidden mode on a UI.

Referring to 1101 of FIG. 11, a region 1110 where a medical tool is located is displayed as a reference region, and at least one distance-indicating line 1120 is displayed with respect to the reference region.

1102 of FIG. 11 shows an operation of the ultrasound imaging apparatus 400 in a distance-indicating line fixed mode. When the user selects, during a medical activity, a distance-indicating line fixed mode and moves the medical tool in a state in which an ultrasound image is displayed as shown in 1101 of FIG. 11, the at least one distance-indicating line 1120 may remain displayed at a position indicated as shown in 1101 of FIG. 11, and a region 1112 where the medical tool is located may be updated and displayed according to movement of the medical tool.

By operating in a distance-indicating line fixed mode, when the at least one distance-indicating line 1120 is being updated and displayed in real-time during a user's medical activity, the ultrasound imaging apparatus 400 may fixedly display the at least one distance-indicating line 1120 in a shape desired by the user while allowing the user to perform the medical activity by identifying movement of the medical tool.

Furthermore, when operating in the distance-indicating line fixed mode, the ultrasound imaging apparatus 400 may display the at least one distance-indicating line 1120 in a shape different from that in the first operation mode. For example, in the distance-indicating line fixed mode, the at least one distance-indicating line 1120 may be displayed as at least one dashed line or in a color different from that in the first operation mode. A method of displaying at least one distance-indicating line in a color different from that in the first operation mode is not limited to the above-described example, and various other methods may be used.

1103 of FIG. 11 shows an operation of the ultrasound imaging apparatus 400 in a distance-indicating line hidden mode. When the user selects, during a medical activity, a distance-indicating line hidden mode in a state in which the ultrasound image is displayed as shown in 1101 of FIG. 11, the at least one distance-indicating line 1120 may not be displayed, and the region 1112 where the medical tool is located may be updated and displayed according to movement of the medical tool.

By operating in a distance-indicating line hidden mode, when the at least one distance-indicating line 1120 is being updated and displayed in real-time during a user's medical activity, the ultrasound imaging apparatus 400 allows the user to clearly identify tissue surrounding the medical tool during a predetermined time period.

Figure 12A:
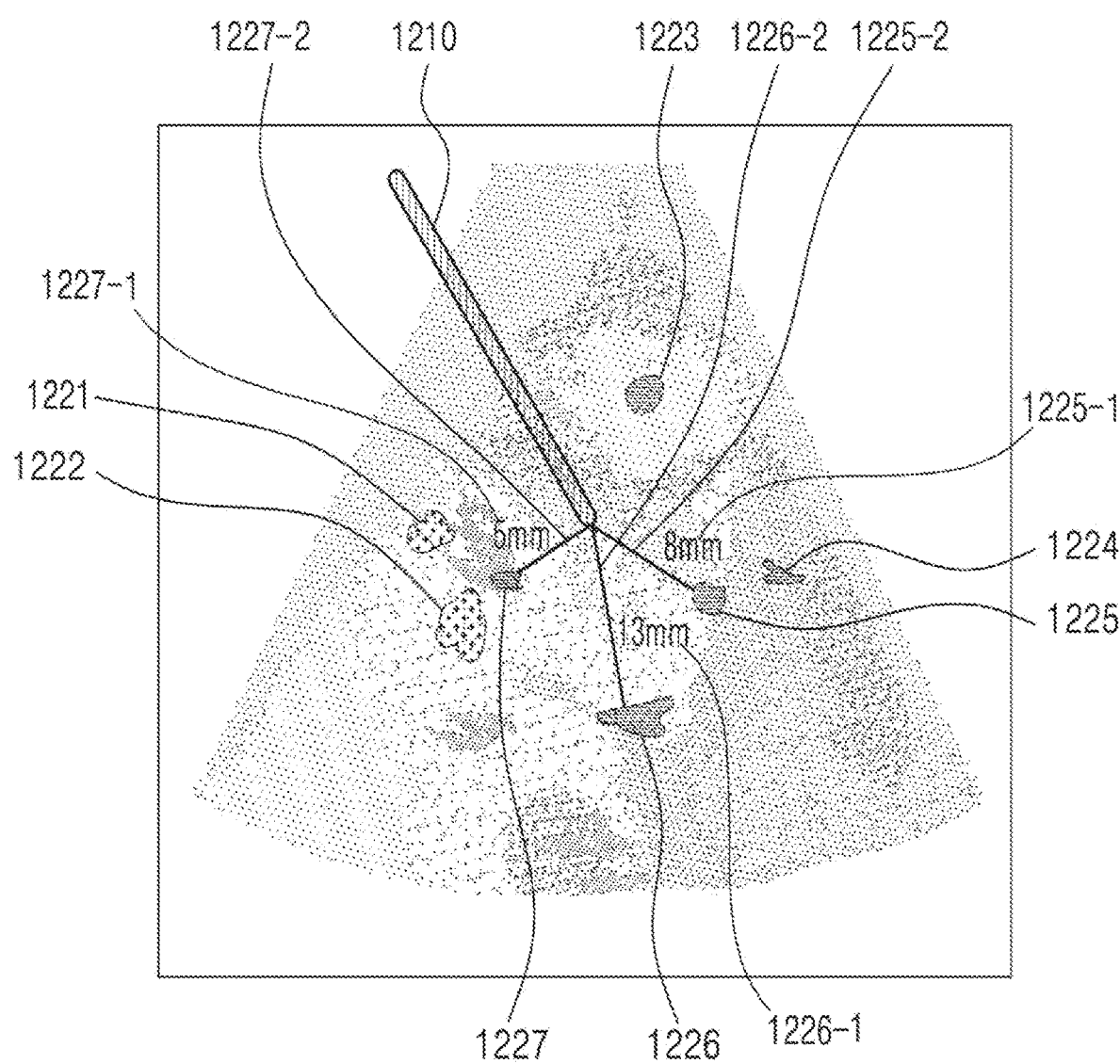
FIGS. 12A and 12B are diagrams for explaining a method, performed by an ultrasound imaging apparatus, of displaying information about a distance from a medical tool to each of at least one region of interest (ROI), according to an embodiment of the disclosure.
Figure 12B:
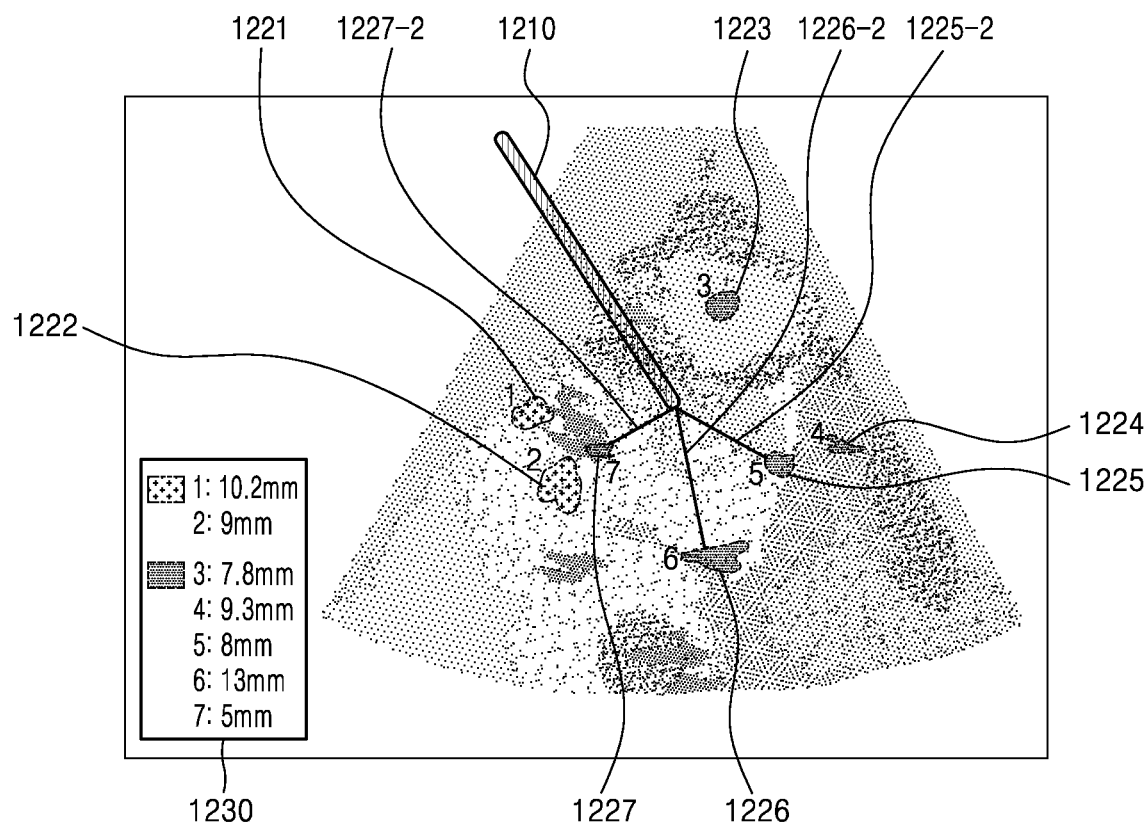

FIGS. 12A and 12B are diagrams for explaining a method, performed by the ultrasound imaging apparatus 400, of displaying information about a distance from a medical tool to each of at least one ROI, according to an embodiment of the disclosure.

An operation mode in which the ultrasound imaging apparatus 400 visually displays a medical tool and at least ROI together with distance information about a distance from the medical tool to each of the at least one ROI is referred to as a 'second operation mode'.

Referring to FIG. 12A, the ultrasound imaging apparatus 400 may visually display a medical tool 1210 and seven (7) ROIs 1221, 1222, 1223, 1224, 1225, 1226, and 1227. Furthermore, the ultrasound imaging apparatus 400 may respectively display pieces of distance information 1225-1, 1226-1 and 1227-1 about corresponding distances from a distal end of a medical tool 1210 for three (3) ROIs 1225 through 1227.

The pieces of distance information 1225-1, 1226-1 and 1227-1 respectively regarding the three ROIs 1225 through 1227 may include lines 1225-2, 1226-2, and 1227-2 respectively connecting the distal end of the medical tool 1210 to the three ROIs 1225 through 1227 with shortest distances and information about the shortest distances.

A method of displaying the pieces of distance information 1225-1, 1226-1, and 1227-1 respectively regarding the three ROIs 1225 through 1227 is not limited to the example shown in FIG. 12A, and various other methods may be used. For example, a distance between the distal end of the medical tool 1210 and a center of each of the ROIs 1221 through 1227 may be displayed instead of displaying a shortest distance therebetween as distance information. Furthermore, the unit of distance being displayed may be determined as various distance units such as mm and cm. Furthermore, only a line connecting the distal end of the medical tool 1210 to each of the ROIs 1221 through 1227 may be displayed without a number indicating a distance therebetween.

Furthermore, referring to FIG. 12B, pieces of distance information may not be displayed near the lines 1225-2, 1226-2, and 1227-2 respectively connecting the distal end of the medical tool 1210 to the corresponding ROIs 1225 through 1227, but may be displayed as a table 1230 representing distance information.

According to an embodiment of the disclosure, the ultrasound imaging apparatus 400 may divide the plurality of ROIs 1221 through 1227 into two groups and visually display the two groups, and the table 1230 may represent distance information regarding the ROIs 1221 through 1227 for each group.

For example, among the ROIs 1221 through 1227 shown in FIG. 12B, the ROIs 1221 and 1222 may be determined as a first group, and the ROIs 1223 through 1227 may be determined as a second group. As shown in FIG. 12B, the first group may be visually displayed differently in an ultrasound image from the second group. In the table 1230 representing the distance information, the distance information may be displayed for each group.

The user may cluster a plurality of ROIs into different groups via a UI provided by the ultrasound imaging apparatus 400.

Although FIGS. 12A and 12B do not show at least one distance-indicating line for convenience, at least one distance-indicating line according to various embodiments of the disclosure may be displayed together with distance information regarding ROIs. In other words, the ultrasound imaging apparatus 400 may perform operations simultaneously in the first and second operation modes.

Figure 13:
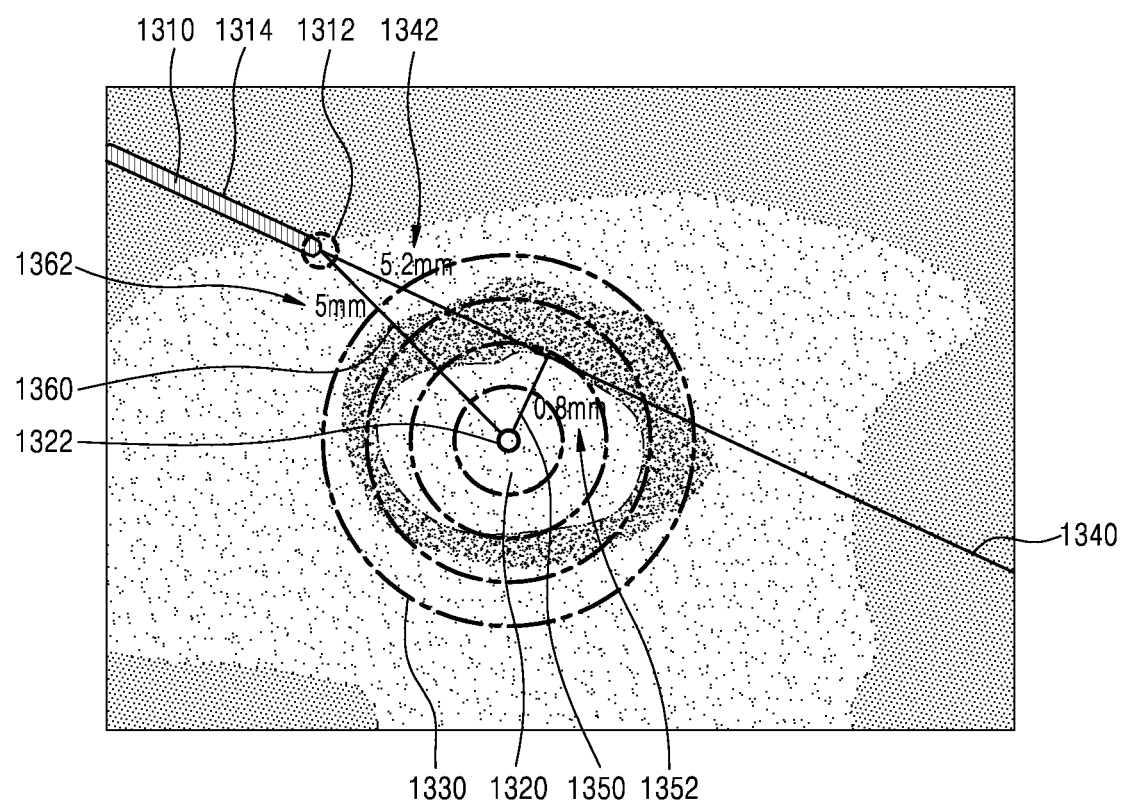
FIG. 13 is a diagram for explaining a method, performed by an ultrasound imaging apparatus, of displaying information about a distance between a medical tool and at least one ROI in various ways, according to an embodiment of the disclosure.

FIG. 13 is a diagram for explaining a method, performed by the ultrasound imaging apparatus 400, of displaying information about a distance between a medical tool and at least one ROI in various ways, according to an embodiment of the disclosure.

Referring to FIG. 13, as described with reference to FIG. 9B, at least one distance line 1330 arranged around a preset region 1322 is displayed in an ultrasound image. The preset region 1322 is a region corresponding to a center of an ROI 1320. Furthermore, a border 1314 of a medical tool 1310 may be visually displayed.

According to an embodiment of the disclosure, the ultrasound imaging apparatus 400 may display an extension line 1340 extending from a distal end 1312 of the medical tool 1310 along (or parallel to) a long axis of the medical tool 1310. In other words, the ultrasound imaging apparatus 400 may display the extension line 1340 extending the long axis of the medical tool 1310.

Furthermore, the ultrasound imaging apparatus 400 may display information about a shortest distance from the extension line 1340 to the preset region 1322 (hereinafter, referred to as a 'first distance 1352'). First distance information may include a line 1350 indicating the first distance 1352 and the first distance 1352.

Furthermore, the ultrasound imaging apparatus 400 may display information about a second distance 1342 that is a distance from the distal end 1312 of the medical tool 1310 to a point where the line 1350 indicating the first distance 1352 and the extension line 1340 meet each other. Second distance information may include a part of the extension line 1340 indicating the second distance 1342 and the second distance 1342.

Furthermore, the ultrasound imaging apparatus 400 may display information about a shortest distance from the distal end 1312 of the medical tool 1310 to the preset region 1322 (hereinafter, referred to as a 'third distance 1362'). Third distance information may include a line 1360 indicating the third distance 1362 and the third distance 1362.

An operation mode in which the ultrasound imaging apparatus 400 displays the first distance information, the second distance information, and the third distance information as described above is referred to as a third operation mode.

By performing an operation in the third operation mode, the ultrasound imaging apparatus 400 allows the user to identify a distance relation between the distal end 1312 of the medical tool 1310 and the preset region 1322 according to various criteria.

In addition, a method, performed by the ultrasound imaging apparatus 400, of displaying the first distance information, the second distance information, and the third distance information is not limited to the example shown in FIG. 13, and various other methods may be used. For example, a line indicating each piece of distance information may be displayed in a different color.

Figure 14:
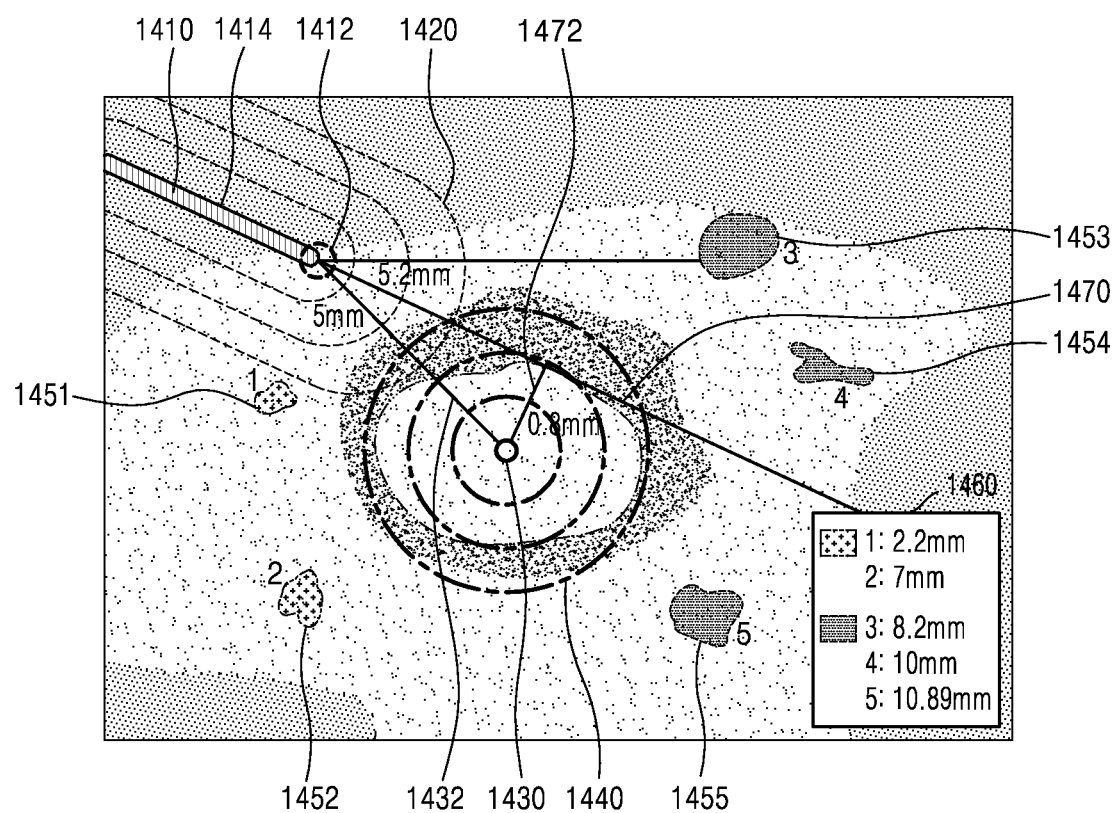
FIG. 14 is a diagram for explaining a method, performed by an ultrasound imaging apparatus, of displaying a distance-indicating line together with distance information, according to an embodiment of the disclosure.

FIG. 14 is a diagram for explaining a method, performed by an ultrasound imaging apparatus, of displaying a distance-indicating line together with distance information, according to an embodiment of the disclosure.

According to an embodiment of the disclosure, the ultrasound imaging apparatus 400 may simultaneously perform operations in the first through third operation modes. In other words, the ultrasound imaging apparatus 400 may display at least one distance-indicating line according to various embodiments of the disclosure described with reference to FIGS. 5 through 13 and distance information simultaneously in an ultrasound image.

Referring to FIG. 14, at least one distance-indicating line 1420 arranged around a medical tool 1410 (including a border 1414) is displayed simultaneously with at least one distance-indicating line 1440 arranged around a preset region 1430. In other words, FIG. 14 shows an operation of the ultrasound imaging apparatus 400 in the first operation mode.

Furthermore, as described with reference to FIG. 12B, lines respectively connecting a distal end 1412 of a medical tool 1410 to five (5) ROIs 1451, 1452, 1453, 1454, and 1455 are displayed. In other words, FIG. 14 shows an operation of the ultrasound imaging apparatus 400 in the second operation mode.

Furthermore, as described with reference to FIG. 13, an extension line 1470 extending a long axis of the medical tool 1410, a line 1472 indicating a shortest distance from the extension line 1470 to the preset region 1430, a line 1432 indicating a shortest distance from the distal end 1412 of the medical tool 1410 to the preset region 1430, etc. are displayed in the ultrasound image. In other words, FIG. 14 shows an operation of the ultrasound imaging apparatus 400 in the third operation mode.

By simultaneously performing operations in the first through third operation modes, the ultrasound imaging apparatus 400 allows the user to identify a distance relation between the medical tool 1410 and tissues of an object in the ultrasound image according to various criteria.

Furthermore, the user may use a UI provided by the ultrasound imaging apparatus 400 to turn on or off at least one of the first through third operation modes.

Embodiments of the disclosure may be implemented through non-transitory computer-readable recording media having stored thereon computer-executable instructions and data. The instructions may be stored in the form of program code, and when executed by a processor, generate a predetermined program module to perform a specific operation. Furthermore, when being executed by the processor, the instructions may perform specific operations according to the embodiments of the disclosure.

What is claimed is:

1. An ultrasound imaging apparatus comprising:
a probe configured to transmit ultrasound signals to an object and receive echo signals corresponding to the ultrasound signals;
a display; and
at least one processor configured to:
detect a reference region of a medical tool configured to be inserted into the object in an ultrasound image generated based on the echo signals; and
control the display to display at least one distance-indicating line arranged with respect to the reference region in the ultrasound image,
wherein the at least one processor is further configured to control the display to display the at least one distance-indicating line, each of the at least one distance-indicating line being at a set interval with respect to the reference region of the medical tool, wherein points on one distance-indicating line of the at least one distance-indicating line have a same distance from the reference region,
wherein the at least one processor is further configured to control the display to display distance information about a distance from the reference region of the medical tool to each of the at least one distance-indicating line,
wherein the at least one processor is further configured to control the display to:
visually display at least one region of interest (ROI) in the ultrasound image; and
display second distance information about the distance from the reference region of the medical tool to each of the at least one ROI,
wherein the at least one processor is further configured to update a position of the at least one distance-indicating line such that a distance between the reference region and the at least one distance-indicating line maintains the set interval according to movement of the medical tool,
wherein the at least one processor is further configured to update the second distance information according to the movement of the medical tool,
wherein the at least one processor is further configured to provide a user interface for setting conditions for respectively setting a number of the at least one distance-indicating line, a characteristic of the at least one distance-indicating line, an interval between the at least one distance-indicating line, and the reference region of the medical tool, and
wherein the characteristic of the at least one distance-indicating line comprises a transparency with respect to a distance of each of the at least one distance-indicating line from the reference region of the medical tool.

2. The ultrasound imaging apparatus of claim 1, wherein the reference region of the medical tool is at least a portion of the medical tool comprising a region where a distal end of the medical tool is located, and
wherein the at least one processor is further configured to control the display to display the at least one distance-indicating line according to its distance from a border of the reference region or from a center of the reference region.

3. The ultrasound imaging apparatus of claim 1, wherein the at least one processor is further configured to control the display to:
visually display the reference region of the medical tool; and fixedly display, in response to reception of an input of fixing a distance-indicating line, the at least one distance-indicating line currently being displayed, regardless of the movement of the medical tool.

4. The ultrasound imaging apparatus of claim 1, wherein the at least one processor is further configured to control the display to:
visually display the reference region of the medical tool; and
hide, in response to reception of an input of hiding a distance-indicating line, the at least one distance-indicating line currently being displayed.

5. The ultrasound imaging apparatus of claim 1, wherein a condition for setting the reference region of the medical tool comprises at least one from among a width, an area, and a shape of the reference region and whether to set the reference region as a dot.

6. The ultrasound imaging apparatus of claim 1, wherein the at least one processor is further configured to control the display to:
display an extension line extending a long axis of the medical tool; and
display at least one of a line connecting a distal end of the medical tool to each of the at least one ROI, third distance information about a distance from the distal end of the medical tool to each of the at least one ROI, and information about a shortest distance from the extension line to each of the at least one ROI.

7. The ultrasound imaging apparatus of claim 1, wherein the at least one processor is further configured to update the position of the at least one distance-indicating line tracking a changed position of the reference region according to the movement of the medical tool.

8. A method of controlling an ultrasound imaging apparatus, the method comprising:
detecting a reference region of a medical tool configured to be inserted into an object in an ultrasound image of the object;
displaying at least one distance-indicating line arranged with respect to the reference region in the ultrasound image;
controlling a display of the ultrasound imaging apparatus to display:
the at least one distance-indicating line, each of the at least one distance-indicating line being at a set interval with respect to the reference region of the medical tool, wherein points on one distance-indicating line of the at least one distance-indicating line have a same distance from the reference region; and
distance information about a distance from the reference region of the medical tool to each of the at least one distance-indicating line;
visually displaying at least one region of interest (ROI) in the ultrasound image;
displaying second distance information about the distance from the reference region of the medical tool to each of the at least one ROI;
updating a position of the at least one distance-indicating line such that a distance between the reference region and the at least one distance-indicating line maintains the set interval according to movement of the medical tool;
updating the second distance information according to the movement of the medical tool; and
providing a user interface for setting conditions for respectively setting a number of the at least one distance-indicating line, a characteristic of the at least one distance-indicating line, an interval between the at least one distance-indicating line, and the reference region of the medical tool,
wherein the characteristic of the at least one distance-indicating line comprises a transparency with respect to a distance of each of the at least one distance-indicating line from the reference region of the medical tool.

9. The method of claim 8, further comprising visually displaying the reference region of the medical tool,
wherein the displaying of the at least one distance-indicating line comprises fixedly displaying, in response to reception of an input of fixing a distance-indicating line, the at least one distance-indicating line currently being displayed, regardless of the movement of the medical tool.

10. The method of claim 8, further comprising:
displaying an extension line extending a long axis of the medical tool; and
displaying at least one of a line connecting a distal end of the medical tool to each of the at least one ROI, third distance information about a distance from the distal end of the medical tool to each of the at least one ROI, and information about a shortest distance from the extension line to each of the at least one ROI.

11. The method of claim 8, further comprising updating the position of the at least one distance-indicating line tracking the reference region according to the movement of the medical tool.

12. A computer program product comprising a non-transitory recording medium having stored therein instructions for:
detecting a reference region of a medical tool configured to be inserted into an object in an ultrasound image of the object;
displaying at least one distance-indicating line arranged with respect to the reference region in the ultrasound image;
wherein the displaying the at least one distance-indicating line comprises:
displaying the at least one distance-indicating line, each of the at least one distance-indicating line being at a set interval with respect to the reference region of the medical tool, wherein points on one distance-indicating line of the at least one distance-indicating line have a same distance from the reference region; and
displaying distance information about a distance from the reference region of the medical tool to each of the at least one distance-indicating line;
visually displaying at least one region of interest (ROI) in the ultrasound image;
displaying second distance information about the distance from the reference region of the medical tool to each of the at least one ROI;
updating a position of the at least one distance-indicating line such that a distance between the reference region and the at least one distance-indicating line maintains the set interval according to movement of the medical tool;
updating the second distance information according to the movement of the medical tool; and
providing a user interface for setting conditions for respectively setting a number of the at least one distance-indicating line, a characteristic of the at least one distance-indicating line, an interval between the at least one distance-indicating line, and the reference region of the medical tool, wherein the characteristic of the at least one distance-indicating line comprises a transparency with respect to a distance of each of the at least one distance-indicating line from the reference region of the medical tool.

\* \* \* \* \*